United States Patent [19]

Guillaumet et al.

[11] Patent Number: 5,420,132
[45] Date of Patent: May 30, 1995

[54] SUBSTITUTED BENZODIOXINS

[75] Inventors: Gérald Guillaumet; Gérard Coudert, both of Orleans; Valérie Thiery, Clery St Andre; Gérard Adam, Le Mesnil le Roi; Jean-Guy Bizot-Espiard, Paris; Bruno Pfeiffer, Eaubonne; Pierre Renard, Versailles, all of France

[73] Assignee: Adir et Compagnie, Courbevoie, France

[21] Appl. No.: 239,034

[22] Filed: May 6, 1994

[30] Foreign Application Priority Data

May 7, 1993 [FR] France .................. 93 05467

[51] Int. Cl.⁶ .............. A61K 31/495; A61K 31/55; A61K 31/54; A61K 31/535; A61K 31/44; A61K 31/445; C07D 401/00; C07D 403/00; C07D 405/00; C07D 295/00; C07D 243/08; C07D 319/14
[52] U.S. Cl. .................. 514/253; 514/212; 514/218; 514/228.2; 514/233.5; 514/278; 514/324; 514/376; 514/452; 544/295; 544/145; 544/359; 544/364; 544/377; 544/360; 544/361; 544/386; 544/391; 544/62; 540/575; 540/596; 546/16; 546/202; 548/232; 549/366
[58] Field of Search .......... 544/364, 377, 360, 361; 549/366; 514/253, 452

[56] References Cited

U.S. PATENT DOCUMENTS

| | | | |
|---|---|---|---|
| 3,117,978 | 1/1964 | Biel | 549/366 |
| 5,036,070 | 7/1991 | Abou-Gharbia | 514/252 |
| 5,120,758 | 6/1992 | Satoh | 514/452 |
| 5,126,366 | 6/1992 | Stack et al. | 514/452 |
| 5,126,367 | 6/1992 | Stack et al. | 514/452 |
| 5,245,051 | 9/1993 | Stack et al. | 549/361 |

FOREIGN PATENT DOCUMENTS 0018675 4/1980 European Pat. Off. .
1843M 4/1962 France .

OTHER PUBLICATIONS

J. Med. Chem., 30, 49–57, (1987), "2,4–Diamino–6,-7–dimethoxyquinazolines. 1 . . . " Campbell, et al.
J. Chem. Soc., 6(B), 1207–1210 (1970), "The Conformational Analysis of Saturated Heterocycles. Part XXVI.¹ 2–Substituted Benzodioxans²", Cook, et al.
J.A.C.S., 77, 5373–5375, (1955), "Derivatives of 1,4–Benzodioxan. I. 1,4–Benzodioxan-2-carboxamides", Koo, et al.
Chemical Abstracts, 70, No. 37744s, (1969).
Chemical Abstracts, 70, No. 96754t, (1969).
Tetrahedron letters, 12, 1059–1062, (1978).

*Primary Examiner*—Cecilia Tsang
*Attorney, Agent, or Firm*—Gordon W. Hueschen

[57] ABSTRACT

A compound of formula (I):

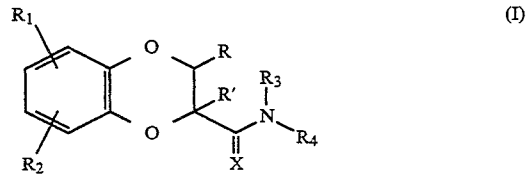

wherein:
  X represents O, S or $H_2$,
  R and R' each represents hydrogen or together form a bond,
  $R_1$, $R_2$, $R_3$ and $R_4$ are as defined in the description.
useful in the treatment or prevention of disorders involving oxidative processes.

12 Claims, No Drawings

SUBSTITUTED BENZODIOXINS

The present invention relates to new substituted benzodioxins, a process for their preparation, and pharmaceutical compositions containing them.

The literature provides numerous examples of substituted 1,4-benzodioxins which are used in various fields.

Patent EP-A-515941 describes 6-(pyrrol-2-yl)benzodioxanes used as pesticides. Patent EP-A-520674 describes N-amino-phenoxy-alkyl-2,3-dihydro-1,4-benzodioxin-2-methanamine compounds which are dopamine agonists.

In their work, (Farmatsiya (Sofia), 27, (5), 1–5, (1977)), Velichkof et al. disclose a method of synthesising N-substituted 1,4-benzodioxane-2,3-dicarboxamides.

The applicant has discovered that certain benzodioxins substituted in the 2-position by a carboxamide, thiocarboxamide or methyleneamine group possess antioxidant properties that are especially valuable pharmacologically.

The applicant has discovered new substituted benzodioxins and their very valuable pharmacological properties based on their ability to inhibit the oxidation of lipids and, especially, lipoproteins.

The invention relates more especially to new substituted benzodioxins of the general formula (I):

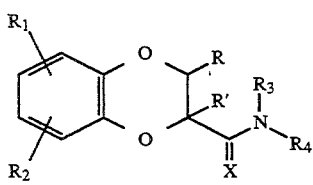

wherein:
- R and R' each represents hydrogen, in the case of 2,3-dihydrobenzodioxins, or together form a bond, in the case of benzodioxins,
- $R_1$ and $R_2$, which are the same or different, are each selected, independently of the other, from hydrogen, alkyl having from 1 to 6 carbon atoms in straight or branched chain, hydroxy, alkoxy having from 1 to 5 carbon atoms in straight or branched chain, a group:

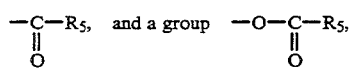

wherein $R_5$ is selected from alkyl having from 1 to 5 carbon atoms in straight or branched chain, optionally substituted aryl selected from phenyl and naphthyl, optionally substituted aralkyl selected from phenyl and naphthyl attached to an alkyl chain having from 1 to 4 carbon atoms, optionally substituted heteroaryl selected from pyridyl, pyrrolyl, pyrazinyl, pyridazinyl, pyrimidinyl, quinolyl, quinazolinyl and indolyl, and optionally substituted heteroarylalkyl selected from the heteroaryl radicals defined above attached to an alkyl chain having from 1 to 4 carbon atoms,
- $R_3$ and $R_4$, which are the same or different, are each selected, independently of the other, from hydrogen, alkyl having from 1 to 5 carbon atoms in straight or branched chain and being optionally substituted, and aryl, aralkyl, heteroaryl and heteroarylalkyl each of which may optionally be substituted by one or more chemical entities selected from the radicals defined for $R_1$ or $R_2$, or $R_3$ and $R_4$, together with the nitrogen atom to which they are attached, form a 15 heterocycle of formula (I')

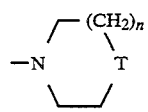

wherein
- n is selected from 0, 1, 2 and 3,
- T is selected from oxygen, the group

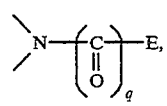

- the group 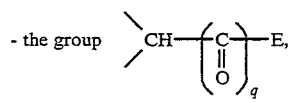

- and the group 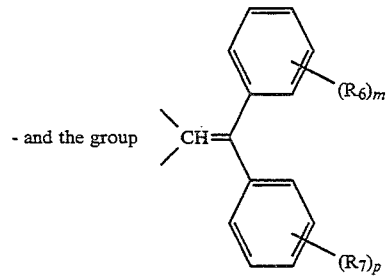

wherein:
- m and p, which are the same or different, each independently represents the value 0, 1, 2, 3, 4 or 5,
- $R_6$ and $R_7$, which are the same or different, are each selected, independently of the other, from halogen, hydroxy, straight-chain or branched alkyl having from 1 to 5 carbon atoms, alkoxy, haloalkyl, and polyhaloalkyl,
- q is selected from 0 and 1,
- E is selected from hydrogen, alkyl having from 1 to 5 carbon atoms in straight or branched chain, aryl, aralkyl, heteroaryl and heteroarylalkyl each of which being as defined hereinbefore and being optionally substituted by one or more radicals $R_6$ as defined hereinbefore, and the group:

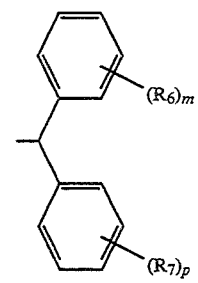

wherein $R_6$, $R_7$, m and p are as defined hereinbefore, with the proviso that, when X=O and $R_1=R_2=H$, T cannot represent $CH_2$ or quinazolinyl-2-yl amino, and X is selected from O, S and $H_2$, it being understood that, unless indicated otherwise, the expression "optionally substituted" indicates an optional substitution by one or more radicals selected from hydroxy, nitro, cyano, alkyl, alkoxy, acyl, haloalkyl, polyhaloalkyl, amino, alkylamino and dialkylamino, the alkyl chains of the alkyl, alkoxy, acyl, haloalkyl, polyhaloalkyl, alkylamino and dialkylamino groups having from 1 to 5 carbon atoms in straight or branched chain, with the following provisos:

when R and R' each represents hydrogen, X cannot represent $H_2$, when R and R' each represents hydrogen and X represents oxygen,
either $R_1$ and $R_2$ are each different from hydrogen,
either $R_1$ is different from hydrogen and $R_3$ and $R_4$, together with the nitrogen atom to which they are attached, form a heterocycle as defined hereinbefore, their possible stereoisomers, N-oxides and pharmaceutically-acceptable addition salts with an acid or a base.

Of the pharmaceutically-acceptable acids that may be used for the formation of an addition salt with the compounds of the invention there may be mentioned, as non-limiting examples, hydrochloric, phosphoric, sulfuric, tartric, citric, maleic, fumaric, alkylsulfonic, arylsulfonic and camphoric acids.

Of the pharmaceutically-acceptable bases that may be used for the formation of an addition salt with the compounds of the invention there may be mentioned, as non-limiting examples, sodium or potassium hydroxide, diethylamine, triethylamine, ethanolamine, diethanolamine, arginine and lysine.

The invention relates also to a process for the preparation of compounds of formula (I) which is characterised in that a cyclisation reaction is carried out in the presence of an alkali metal carbonate, for example potassium carbonate, in an aprotic solvent, such as acetone, at reflux, starting from catechol and alkyl 2,3-dibromopropionate, resulting in a compound of formula (IIa):

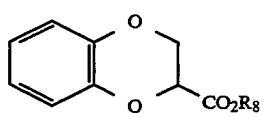
(IIa)

wherein $R_8$ represents an alkyl radical containing from 1 to 5 carbon atoms in straight or branched chain, which is optionally subjected to an acylation reaction with an acylating agent of formula (III):

(III)

wherein $R_5$ is as defined hereinbefore, with a Lewis acid, such as aluminium chloride in carbon disulfide at 0° C., to yield a compound of formula (IIb):

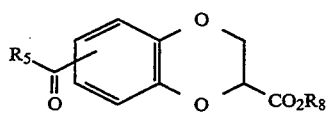
(IIb)

wherein $R_5$ and $R_8$ are as defined hereinbefore, which may optionally be oxidised to the corresponding diester of formula (IIc):

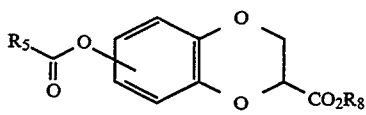
(IIc)

wherein $R_5$ and $R_8$ are as defined hereinbefore, by means of an oxidising agent, for example meta-chloro-perbenzoic acid in methylene chloride, and then optionally converted, by the action of an alkali metal alcoholate, for example sodium ethanolate in methanol, to the phenol of formula (IId):

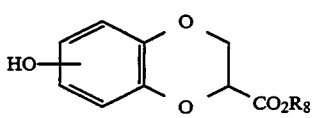
(IId)

wherein $R_8$ is as defined hereinbefore, it being possible for the keto esters of formula (IIb) on the other hand to be hydrogenated, by the action of hydrogen and palladium, to a compound of formula (IIe):

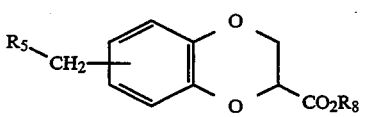
(IIe)

wherein $R_5$ and $R_8$ are as defined hereinbefore, it being possible for the phenol of formula (IId) to be etherified by reaction with a halogenated compound of formula (IV):

$R_5$-Hal (IV)

wherein Hal is a halogen atom, to yield a compound of formula (IIf):

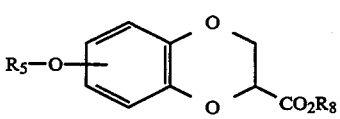
(IIf)

wherein $R_5$ and $R_8$ are as defined hereinbefore, or acylated by an acyl chloride of formula 0ID as defined hereinbefore, to yield a diester of formula (IIc) as defined hereinbefore, the compounds of formulae (IIa) to (Iif) forming the totality of the compounds of formula (II):

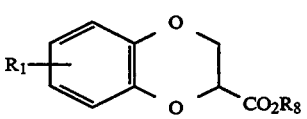
(II)

wherein $R_1$ and $R_8$ are as defined hereinbefore, which may again be treated like the compounds of formula (IIa) to (IIf) or in acidic medium with a tertiary alcohol of formula (X):

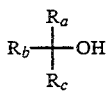
(Va)

wherein $R_a$, $R_b$ and $R_c$ each independently represent a straight-chain or branched alkyl radical containing from 1 to 3 carbon atoms, to yield compounds of formula (Va):

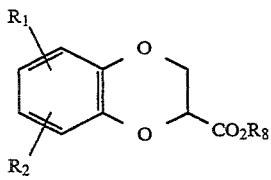
(Va)

wherein $R_1$, $R_2$ and $R_8$ are as defined hereinbefore, it being possible for the benzodioxanes of formula (Va) optionally to be treated with a brominating agent, such as N-bromosuccinimide in carbon tetrachloride, in the presence of a radical initiator, such as azo-bis-isobutyronitrile, to yield an intermediate of formula (VI):

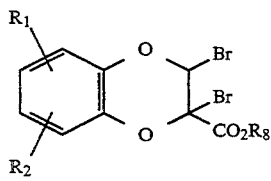
(VI)

wherein $R_1$, $R_2$ and $R_8$ are as defined hereinbefore, which is then exposed to an alkali metal halide, such as sodium iodide in acetone, to yield the corresponding benzodioxins of formula (Vb):

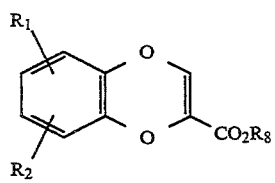
(Vb)

wherein $R_1$, $R_2$ and $R_8$ are as defined hereinbefore, the compounds of formula (Va) and (Vb) forming the totality of the compounds of formula (V)

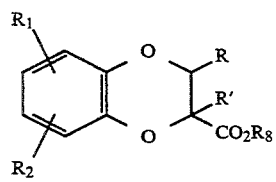
(V)

wherein $R_1$, $R_2$, $R_8$, R and R' are as defined hereinbefore, which are finally hydrolysed to yield the acids of formula (VII):

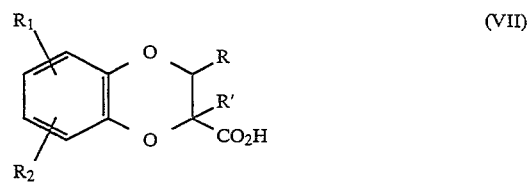
(VII)

wherein R, R', $R_1$ and $R_2$ are as defined hereinbefore, which are subjected to a peptide coupling reaction at 0° C., in the presence of 1-(3-dimethylaminopropyl)-3-ethylcarbodiimide, (EDCI) and hydroxybenzotriazole (HOBt) in dimethylformamide, with an amine of formula (VIII):

(VIII)

wherein $R_3$ and $R_4$ are as defined hereinbefore, that reaction yielding compounds of formula (IXa):

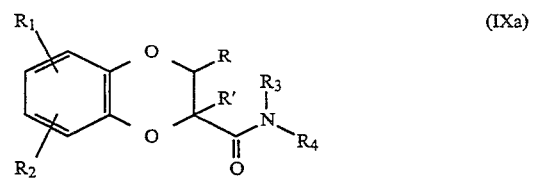
(IXa)

wherein $R_1$, $R_2$, $R_3$, $R_4$, R and R' are as defined hereinbefore, a particular instance of compounds of formula (I) wherein X represents oxygen, which are either:

converted by treatment of the corresponding amide with Lawesson's reagent into a thioamide of formula (IXb):

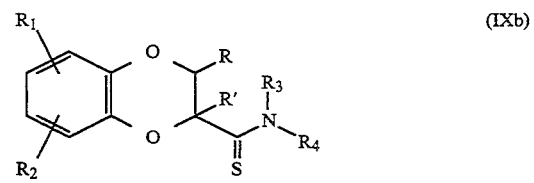
(IXb)

wherein $R_1$, $R_2$, $R_3$, $R_4$, R and R' are as defined hereinbefore, a particular instance of compounds of formula (I) wherein X represents sulfur, or converted by reduction of the corresponding amide with a reducing agent, such as lithium aluminium hydride, in an aprotic anhydrous solvent, such as diethyl ether, to compounds of formula (IXc):

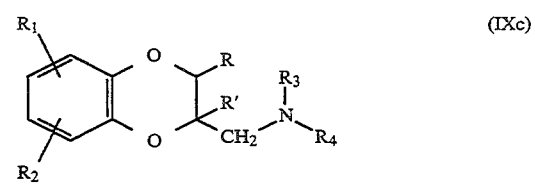
(IXc)

wherein $R_1$, $R_2$, $R_3$, $R_4$, R and R' are as defined hereinbefore, a particular instance of compounds of formula (I) wherein X represents the group $H_2$, the totality of the compounds of formula (IXa), (IXb)

and (IXc) forming the totality of the compounds of formula (I), which are purified and optionally separated into their stereoisomers by a conventional method of separation and, if desired, converted into their pharmaceutically acceptable addition salts with an acid or a base.

The compounds of formula (I) wherein $R_3$ and $R_4$ each represents hydrogen may also be prepared directly, by the action of an ammonium hydroxide solution in ethanol on compounds of formula (V).

The compounds of the present invention have very significant antioxidant properties. Pharmacological studies have in particular demonstrated that the compounds of the present invention exhibit remarkable protective activities within the framework of peroxidation processes of lipids and, especially, lipoproteins. The activities of the compounds of the invention are in particular far superior to those of probucol, a commercially available compound known for its antioxidant property and used therapeutically.

Pharmacological studies have also made it possible to demonstrate a strong protective activity in respect of cells placed under oxidising conditions. Finally, the compounds of the invention have exhibited a remarkable antihypoxic activity in vivo in mice at doses that are very distinctly lower than those of vincamine which is used as reference product. The compounds of the present invention, which exhibit antioxidant properties, LDL protecting properties, lipid peroxidation inhibiting properties and a remarkable protection of cellular integrity, may therefore be expected to have an especially beneficial effect in the treatment or prevention of disorders involving oxidative processes and especially ischaemic disorders, metabolic disorders, atheroma, arteriosclerosis, in cerebrovascular and cardiovascular protection, and in the treatment or prevention of damage resulting from surgical trauma and the reperfusion of organs.

The compounds of the invention have also demonstrated an anticalcic activity and exhibit a platelet anti-aggregation activity.

The compounds of formula (I) can thus be used to obtain medicaments that are useful in the treatment or prevention of disorders due to or associated with peroxidation phenomena, in the treatment of ischaemic disorders, metabolic disorders, atheroma and arteriosclerosis, in cerebrovascular and cardiovascular protection, and in the prevention and treatment of damage resulting from surgical trauma and the reperfusion of organs.

The invention relates also to pharmaceutical compositions comprising a compound of formula I or a pharmaceutically acceptable addition salt thereof with an acid or base, alone or in combination with one or more inert, non-toxic excipients. Of the pharmaceutical compositions according to the invention there may be mentioned more especially those which are suitable for oral, parenteral, nasal, rectal, perlingual, ocular or pulmonary administration, and especially injectable preparations, aerosols, eye or nose drops, tablets, film-coated tablets, dragées, soft gelatin capsules, hard gelatin capsules, creams, ointments, dermal gels ...

The dosage used varies in accordance with the age and weight of the patient, the route of administration, the nature of the disorder and any associated treatments, and ranges from 0.5 mg to 2 g per 24 hours. The following Examples illustrate the invention without, however, in any way limiting it. The starting materials are readily available or are prepared by known methods of operation.

PREPARATION 1: ETHYL 2,3-DIHYDRO-1,4-BENZODIOXIN-2-CARBOXYLATE

Under a nitrogen atmosphere, add 18.2 g (131 mmol) of dry potassium carbonate and 13 g (50 mmol) of ethyl 2,3-dibromopropionate in succession to a solution of 20 g (18 1 mmol) of catechol dissolved in 120 cm³ of anhydrous acetone. The operation is repeated four times in succession at intervals of 15 minutes. The reaction mixture is heated at reflux for 18 hours, and then cooled and filtered through Celite. The filtrate is concentrated to a residual volume of 60 cm³, then hydrolysed with 80 cm³ of water and extracted with diethyl ether. After drying over magnesium sulfate, the ethereal phase is concentrated under reduced pressure and the crude product is purified by distillation under reduced pressure (b.p.=155° C. under 15 mm Hg). Ethyl 2,3-dihydro-1,4-benzodioxin-2-carboxylate is thereby obtained in a yield of 80%. $n_D^{25}=1.5214$

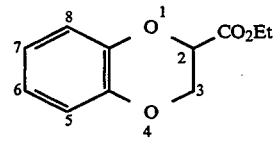

¹H RMN (CDCl₃), δ (ppm): 1.27 (t, 3H, CH₂CH₃, J=6.95 Hz); 4.25 (q, 2H, CH₂CH₃, J=6.95 Hz); 4.35 (d, 2H, H3a, H3b, J₃,₂=3.79 Hz); 4.79 (t, 1H, H₂, J₂,₃=3.79 Hz); 6.86–7.0 (m, 4H$_{aromatic\ protons}$).

PREPARATION 2: ETHYL 6-ACETYL-1,4-BENZODIOXIN-2-CARBOXYLATE

Step 1: Ethyl 2,3-dibromo-1,4-benzodioxin-2-carboxylate

Heat at reflux for 6 hours, under a nitrogen atmosphere, a mixture of 8 g (38.5 mmol) of ethyl 2,3-dihydro-1,4-benzodioxin-2-carboxylate, 15 g (84.5 mmol) of N-bromosuccinimide, and a spatula tip of 2,2'-azobis-(2-methylpropionitrile) in 120 cm³ of carbon tetrachloride. After cooling the reaction mixture and removing the succinimide that has formed, the expected product is isolated by concentrating to dryness. Ethyl 2,3-dibromo-1,4-benzodioxin-2-carboxylate is thereby obtained in a quantitative yield.

Melting point: 102° C.

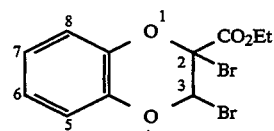

¹H RMN (CDCl₃), δ (ppm): 1.43 (t, 3H, CH₂CH₃, J=6.71 Hz); 4.41–4.56 (m, 2H, CH₂CH₃); 6.94 (s, 1H, H₃); 7.1–7.3 (m, 4H$_{aromatic\ protons}$).

Step 2: Ethyl 1,4-benzodioxin-2-carboxylate

Stir for 3 hours, at room temperature and under a nitrogen atmosphere, a mixture of 16 g (43.7 mmol) of ethyl 2,3-dibromo-1,4-benzodioxin-2-carboxylate and 24 g (160 mmol) of sodium iodide in 80 cm³ of anhydrous acetone. The reaction mixture is then concentrated under reduced pressure, hydrolysed with 80 cm³ of water, and subsequently extracted with diethyl ether.

After treatment with an aqueous sodium thiosulfate solution followed by drying over magnesium sulfate, the ethereal phase is concentrated to dryness under reduced pressure and the crude product is purified by chromatography on a silica column (eluant:petroleum ether/diethyl ether, 40:60). Ethyl 1,4-benzodioxin-2-carboxylate is thereby obtained in a yield of 85%.

Melting point: 42° C.

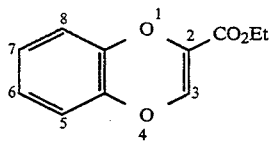

$^1$H RMN (CDCl$_3$), δ (ppm): 1.33 (t, 3H, CH$_2$CH$_3$, J=7.2 Hz); 4.26 (q, 2H, CH$_2$CH$_3$, J=7.2 Hz); 6.67–6.93 (m, 4H$_{aromatic\ protons}$); 6.94 (s, 1H, H$_3$).

Step 3: Ethyl 6-acetyl-1,4-benzodioxin-2-carboxylate

Slowly add 8.1 g (60.7 mmol) of aluminium chloride to a solution of 2.85 g (36.3 mmol) of acetyl chloride and 5 g (24.7 mmol) of ethyl 1,4-benzodioxin-2-carboxylate in 120 cm$^3$ of carbon disulfide at 0° C. Stir for 4 hours at room temperature and then, after acid hydrolysis with 20 cm$^3$ of 2N hydrochloric acid, extract the reaction mixture with methylene chloride. After drying the methylene chloride phase over magnesium sulfate, concentrating to dryness and washing with ethanol, ethyl 6-acetyl-1,4-benzodioxin-2-carboxylate is obtained in a yield of 95%.

Melting point: 122° C.

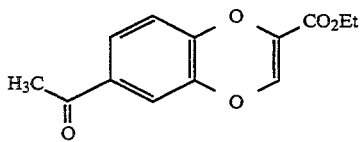

$^1$H RMN (CDCl$_3$), δ (ppm): 1.34 (t, 3H, CH$_2$CH$_3$, J=7.1 Hz); 2.51 (s, 3H, CH$_3$CO); 4.29 (q, 2H, CH$_2$CH$_3$, J=7.1 Hz); 6.87 (d, 1H, H$_8$, J$_{8,7}$=8.69 Hz); 7.31 (d, 1H, H$_5$, J$_{5,7}$=2.37 Hz); 7.53 (dd, 1H, H$_7$, J$_{7,8}$=8.69 Hz, J$_{7,5}$=2.37 Hz).

PREPARATION 3: ETHYL 6-ETHYL-2,3-DIHYDRO-1,4-BENZODIOXIN-2-CARBOXYLATE

Hydrogenate a solution of 3 g of ethyl 6-acetyl-1,4-benzodioxin-2-carboxylate in 15 cm$^3$ of acetic acid under hydrogen pressure (50 psi) in the presence of 0.750 g of 5% palladium on carbon. The crude product obtained by concentrating to dryness is purified by chromatography on a silica column (eluant: petroleum ether/diethyl ether, 70:30). Ethyl 6-ethyl-2,3-dihydro-1,4-benzodioxin-2-carboxylate is thereby obtained in a yield of 70%.

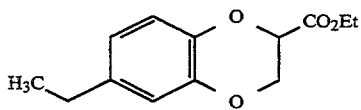

$^1$H RMN (CDCl$_3$) δ (ppm): 6.92 (d, 1H, H$_8$, J$_{8,7}$=8.69 Hz); 6.74–6.70 (m, 2H, H$_7$, H$_5$, J$_{7,8}$=8.69 Hz, J$_{5,7}$=1.58 Hz); 4.79 (t, 1H, H$_2$, J$_{2,3}$=3.95 Hz); 4.38–4.36 (m, 2H, H$_{3a}$, H$_{3b}$); 4.28 (q, 2H, J=7.11 Hz, OCH$_2$CH$_3$); 2.56 (q, 2H, J=7.50 Hz, CH$_3$—CH$_2$—Ar); 1.3 (t, 3H, J=7.11 Hz, OCH$_2$CH$_3$); 1.2 (t, 3H, J=7.50 Hz, CH$_3$CH$_2$Ar).

PREPARATION 4: ETHYL 6-ACETYL-2,3-DIHYDRO-1,4-BENZODIOXIN-2-CARBOXYLATE

Method A

Add 2 g (8.5 mmol) of ethyl 6-ethyl-2,3-dihydro-1,4-benzodioxin-2-carboxylate dissolved in 5 cm$^3$ of anhydrous methylene chloride to a mixture at 0° C. of 0.042 g (0.42 mmol) of chromium trioxide and 5.35 g (59.3 mmol) of 70% tert-butyl hydroperoxide in 30 cm$^3$ of methylene chloride. Stir for 2 hours at 0° C. and then for 72 hours at room temperature. The crude product obtained by concentrating to dryness is purified by chromatography on a silica column (eluant: methylene chloride). Ethyl 6-acetyl-2,3-dihydro-1,4-benzodioxin-2-carboxylate is thereby obtained in a yield of 62%.

Melting point: 60° C.

Method B

Preparation of the complex Ag(Py)$_4$S$_2$O$_8$

Add together a solution composed of 1.6 g of silver nitrate, 32 cm$^3$ of water and 14 cm$^3$ of pyridine and an aqueous solution of 20 g of K$_2$S$_2$O$_8$ in 1350 cm$^3$ of water. The complex which precipitates is isolated by filtration and dried before being used.

Heat at reflux for 3 hours a mixture of 1 g of ethyl 6-ethyl-2,3-dihydro-1,4-benzodioxin-2-carboxylate and 7.85 g of Ag(Py)$_4$S$_2$O$_8$ complex in 20 cm$^3$ of anhydrous acetonitrile. After cooling the mixture, then removing insoluble material by filtration and concentrating the filtrate under reduced pressure, the crude product obtained is purified by chromatography on a silica column silica (eluant:petroleum ether/ethyl acetate, 80:20). Ethyl 6-acetyl-2,3-dihydro-1,4-benzodioxin-2-carboxylate is thereby obtained in a yield of 78%.

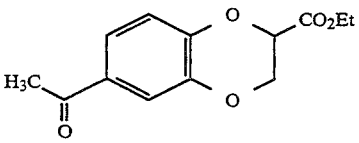

$^1$H RMN (CDCl$_3$), δ (ppm): 7.56 (d, 1H, H$_5$, J$_{5,7}$=1.89 Hz); 7.52 (dd, 1H, H$_7$, J$_{7,8}$=8.05 Hz, J$_{7,5}$=1.89 Hz); 7.05 (d, 1H, H$_8$, J$_{8,78}$.05 Hz); 4.88 (t, 1H, H$_2$, J$_{2,3}$=3.55 Hz); 4.41 (q split, 2H, H$_{3a}$, H$_{3b}$, J$_{3,2}$=3.55 Hz, J$_{3a,3b}$=11.85 Hz); 4.27 (q, 2H, J=7.35 Hz, CH$_2$CH$_3$); 2.53 (s, 3H, CH$_3$CO); 1.27 (t, 3H, J=7.35 Hz, CH$_2$CH$_3$).

PREPARATION 5: 7-ACETYL-2,3-DIHYDRO-1,4-BENZODIOXIN-2-CARBOXAMIDE

Step 1: Ethyl (6 and 7)-acetyl-2,3-dihydro-1,4-benzodioxin-2-carboxylate

Under a nitrogen atmosphere, add 4.5 g (57.7 mmol) of acetyl chloride to a solution of 8 g (38.5 mmol) of ethyl 2,3-dihydro-1,4-benzodioxin-2-carboxylate in 60 cm$^3$ of carbon disulfide. Cool the mixture to 0° C. and then slowly introduce 12.85 g (96.4 mmol) of aluminium chloride. Stir for 4 hours at room temperature and then hydrolyse with 20 cm$^3$ of an iced solution of 2N hydrochloric acid and extract with methylene chloride. The crude product obtained by concentration to dryness is purified by chromatography on a silica column (eluant: petroleum ether/diethyl ether, 40:60). A mixture of ethyl 6-acetyl- and ethyl 7-acetyl-2,3-dihydro-1,4-benzodioxin-2-carboxylate is thereby obtained in a yield of 80%.

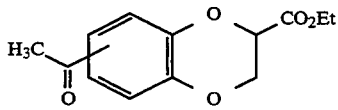

1H NMR (CDCl₃), δ (ppm): 7.64–7.5 (m, 4H, H₇isomer (2-6), H₅isomer (2-6), H₆isomer (2-7), H₈isomer(2-7)); 7.06 (d, 1H, H₈, J₈,₇=8.29 Hz); 6.92 (d, 1H, H₅, J₅,₆=8.29 Hz); 4.92–4.82 (m, 2H, H₂isomers (2-6) and (2-7)); 4.52–4.38 (m, 4H, 2×H₃ₐ,H₃ᵦ); 4.28 (q, 4H, 2×CH₂CH₃, J=7.1 Hz); 2.54 (s, 3H, CH₃COisomer(2-7)); 2.53 (s, 3H, CH₃COisomer(2-6)); 1.29 (t, 6H, 2×CH₂CH₃, J=7.1 Hz).

Step 2:
7-Acetyl-2,3-dihydro-1,4-benzodioxin-2-carboxamide

Stir a solution of 8 g of the mixture of ethyl (6 and 7)-acetyl-2,3-dihydro-1,4-benzodioxin-2-carboxylate in a mixture of ethanol and ammonia (3: 1) for 8 hours at room temperature. The 7-acetyl-2,3-dihydro-1,4-benzodioxin-2-carboxamide precipitates from the reaction mixture whereas the 6-acetyl-2,3-dihydro-1,4-benzodioxin-2-carboxamide remains in solution. After isolation by filtration and recrystallisation from 70% ethanol, the 7-acetyl-2,3-dihydro-1,4-benzodioxin-2-carboxamide is isolated in a yield of 50%.

Melting point: 212° C.

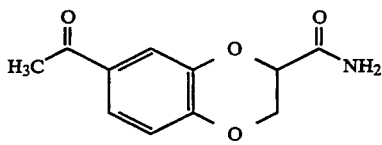

¹H NMR (CDCl₃) δ (ppm): 2.5 (s, 3H, CH₃CO); 4.36 (d, 2H, H₃ₐ, H₃ᵦ, J=3.95 Hz); 4.82 (t, 1H, H₂, J₂,₃=3.95 Hz); 6.97 (d, 1H, H₅, J₅,₆=,8.29 Hz); 7.47–7.55 (m, 2H, H₈, H₆); 7.61 (s broad, 2H, CONH₂)

PREPARATION 6: ETHYL 7-ACETYL-2,3-DIHYDRO-1,4-BENZODIOXIN-2-CARBOXYLATE Heat a solution of 3 g (13.5 mmol) of 7-acetyl-2,3-dihydro-1,4-benzodioxin-2-carboxamide dissolved in 100 cm³ of ethanol saturated with hydrochloric acid at reflux for 18 hours under a nitrogen atmosphere. After cooling, the reaction mixture is filtered, concentrated and, after neutralisation with sodium hydrogen carbonate, extracted with methylene chloride. The crude product obtained by concentrating the organic phase to dryness is purified by chromatography on a silica column (eluant: petroleum ether/diethyl ether, 50:50). Ethyl 7-acetyl-2,3-dihydro-1,4-benzodioxin-2-carboxylate is thereby obtained in a yield of 75%.

Melting point: 57° C.

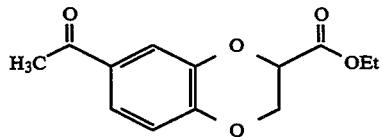

¹H NMR (CDCl₃), δ (ppm): 1.28 (t, 3H, CH₂CH₃, J=6.9 Hz); 2.53 (s, 3H, CH₃CO); 4.28 (q split, 2H, CH₂CH₃, J=6.9 H₂); 4.4–4.5 (m, 2H, H₃ₐ, H₃ᵦ); 4.86 (t, 1H, H₂, J₂,₃=3.55 Hz); 6.92 (d, 1H, H₅, J₅,₆=8.69 Hz); 7.52 (dd, 1H, H₆, J₆,₈=1.97 Hz, J₆,₅=8.69 Hz); 7.63 (d, 1H, H₈, J₈,₆=1.97 Hz).

PREPARATION 7: ETHYL 7-ACETOXY-2,3-DIHYDRO-1,4-BENZODIOXIN-2-CARBOXYLATE

Heat a solution of 2 g (8 mmol) of ethyl 7-acetyl-2,3-dihydro-1,4-benzodioxin-2-carboxylate and 3.05 g (17.7 mmol) of meta-chloro-perbenzoic acid in 30 cm³ of methylene chloride at 50° C. for 18 hours under a nitrogen atmosphere. After cooling, removing by filtration the benzoic acid formed, and washings with aqueous solutions of sodium hydrogen carbonate and then sodium chloride, the reaction mixture is concentrated to dryness under reduced pressure and the crude product obtained is purified by chromatography on a silica column (eluant:petroleum ether/diethyl ether, 70:30). Ethyl 7-acetoxy-2,3-dihydro-1,4-benzodioxin-2-carboxylate is thereby obtained in a yield of 75%.

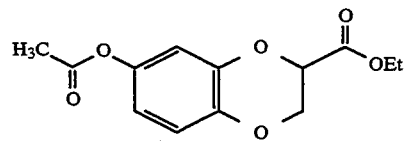

¹H NMR (CDCl₃), δ (ppm): 1.2 (t, 3H, CH₂CH₃); 2.26 (s, 3H, CH₃CO); 4.27 (q, 2H, CH₂CH₃, J=7.1 Hz); 4.37 (d, 2H, H₃ₐ, H₃ᵦ, J₂,₃=3.5 Hz); 4.83 (t, 1H, H₂, J=1.5 Hz); 6,6 (dd, 1H, H₆, J₆,₅=8.2 Hz, J₆,₈=3.16 Hz); 6.78 (d, 1H, H₈, J₈,₆=3.16 Hz); 6.84 (d, 1H, H₅, J₅,₆=8.2 Hz).

PREPARATION 8: ETHYL 6-ACETOXY-2,3-DIHYDRO-1,4-BENZODIOXIN-2-CARBOXYLATE

The ethyl 6-acetoxy-2,3-dihydro-1,4-benzodioxin-2-carboxylate is obtained in a yield of 77% starting from ethyl 6-acetyl-2,3-dihydro-1,4-benzodioxin-2-carboxylate and proceeding as in Preparation 7.

Melting point: 66° C.

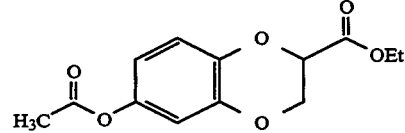

¹H NMR (CDCl₃), δ (ppm): 6.97 (d, 1H, H₈, J₈,₇=8.53 Hz); 6.67–6.58 (m, 2H, H₇, H₅, J₅,₇=2.37 Hz); 4.75 (t, 1H, H₂, J₂,₃=3.55 Hz); 4.37 (d, 2H, H₃ₐ, H₃ᵦ, J₃,₂=3.55 Hz); 4.27 (q split, 2H, J=7.11 Hz, CH₂CH₃); 2.22 (s, 3H, CH₃CO); 1.26 (t, 3H, J=7.11 Hz, CH₃CH₂).

PREPARATION 9: ETHYL 7-ACETOXY-1,4-BENZODIOXIN-2-CARBOXYLATE

Step 1: Ethyl 7-acetoxy-2,3-dibromo-1,4-benzodioxin-2-carboxylate

By proceeding as in Step 1 of Preparation 2, but starting from ethyl 7-acetoxy-2,3-dihydro-1,4-benzodioxin-2-carboxylate, ethyl 7-acetoxy-2,3-dibromo-1,4-benzodioxin-2-carboxylate is obtained in an almost quantitative yield.

Melting point: 131 ° C.

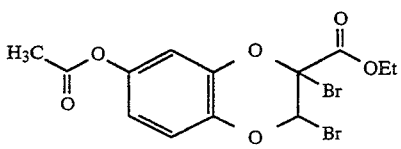

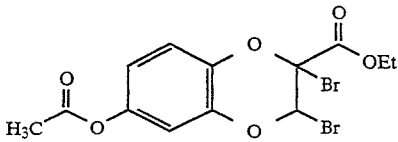

Step 2: Ethyl 7-acetoxy-1,4-benzodioxin -2-carboxylate

By proceeding as in Step 2 of Preparation 2, but starting from ethyl 7-acetoxy-2,3-dibromo-1,4-benzodioxin-2-carboxylate, ethyl 7-acetoxy-1,4-benzodioxin-2-carboxylate is obtained in a yield of 85%.

Melting point: 66° C.

Step 3: Ethyl 6-acetoxy-1,4-benzodioxin-2-carboxylate

By proceeding as for Preparation 9, Step 2, but starting from ethyl 6-acetoxy-2,3-dibromo-1,4-benzodioxin-2-carboxylate, ethyl 6-acetoxy-1,4-benzodioxin-2-carboxylate is obtained in a yield of 80%.

Melting point: 88° C.

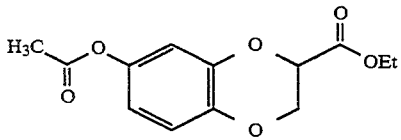

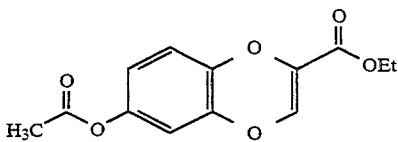

$^1$H NMR (CDCl$_3$) δ (ppm): 1.33 (t, 3H, CH$_2$CH$_3$); 2.26 (s, 3H, CH$_3$COO); 4.27 (q, 2H, CH$_2$CH$_3$, J=7.11 Hz); 6.71–6.58 (m, 3H, H$_8$, H$_6$, H$_5$); 6.94 (s, 1H, H$_3$).

PREPARATION 10: ETHYL 6-ACETOXY-1,4-BENZODIOXIN-2-CARBOXYLATE

Step 1: Ethyl 6-acetyl-2,3-dibromo-1,4-benzodioxin-2-carboxylate

Add a solution of 0.543 cm$^3$ (10.6 mmol) of bromine in 3 cm$^3$ of carbon tetrachloride dropwise, at 0° C., to 2.5 g (10.1 mmol) of ethyl 6-acetyl-1,4-benzodioxin-2-carboxylate partially dissolved in 35 cm$^3$ of carbon tetrachloride. Continue stirring at 0° C. for 2 hours and then concentrate under reduced pressure and purify the resulting crude product by chromatography on a silica column (eluant: petroleum ether/diethyl ether, 60:40). Ethyl 6-acetyl-2,3-dibromo-1,4-benzodioxin-2-carboxylate is thereby obtained in a yield of 92%.

$^1$H NMR (CDCl$_3$); δ (ppm): 6.93 (s, 1H, H$_3$); 6.82 (d, 1H, H$_8$, J$_{8,7}$=7.7 Hz); 6.62 (dd, 1H, H$_7$, J$_{7,8}$=7.7 Hz, J$_{7,5}$=2.56 Hz); 6.51 (d, 1H, H$_5$, J$_{5,7}$=2.56 Hz); 4.29 (q, 2H, J=7.2 Hz, CH$_2$CH$_3$); 2.26 (s, 3H, CH$_3$COO); 1.34 (t, 3H, J=7.2 Hz, CH$_3$CH$_2$).

PREPARATION 11: ETHYL 7-HYDROXY-6-TERT-BUTYL-1,4-BENZODIOXIN-2-CARBOXYLATE

Step 1: Ethyl 7-hydroxy-1,4-benzodioxin-2-carboxylate

Add 0.5 cm$^3$ of a molar solution of sodium ethanolate in ethanol to a solution of 1 g (3.78 mmol) of ethyl 7-acetoxy-1,4-benzodioxin-2-carboxylate in 15 cm$^3$ of anhydrous ethanol under a nitrogen atmosphere. Stir for 18 hours at room temperature and then neutralise with Dowex X-8 resin, acid form, which has been washed beforehand with ethanol. After filtration and concentration to dryness under partial pressure, the crude product obtained is purified by chromatography on a silica column (eluant: petroleum ether/diethyl ether, 80:20). Ethyl 7-hydroxy-1,4-benzodioxin-2-carboxylate is thereby obtained in a yield of 96%.

Melting point: 160° C.

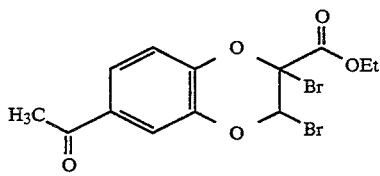

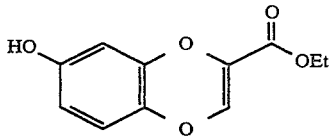

$^1$H NMR (CDCl$_3$), δ (ppm): 7.77 (rid, 1H, H$_7$, J$_{7,8}$=8.29 Hz, J$_{7,5}$=1.97 Hz); 7.70 (d, 1H, H$_5$, J$_{5,7}$=1.97 Hz); 7.27 (d, 1H, H$_8$, J$_{8,7}$=8.29 Hz); 6.49 (s, 1H, H$_3$); 4.54–4.41 (m, 2H, CH$_2$CH$_3$); 2.59 (s, 3H, CH$_3$CO); 1.44 (t, 3H, J=7.34 Hz, CH$_3$CH$_2$).

Step 2: Ethyl 6-acetoxy-2,3-dibromo-1,4-benzodioxin-2-carboxylate

By proceeding as for Preparation 7, but starting from ethyl 6-acetyl-2,3-dibromo-1,4-benzodioxin-2-carboxylate, ethyl 6-acetoxy-2,3-dibromo-1,4-benzodioxin-2-carboxylate is obtained in a yield of 77%.

Melting point: 58° C.

$^1$H NMR (DMSO), δ (ppm): 9.54 (s, 1H, OH); 7.22 (s, 1H, H$_3$); 6.66 (d, 1H, H$_5$, J$_{5,6}$=8.69 Hz); 6.29 (dd, 1H, H$_6$, J$_{6,5}$=8.69 Hz, J$_{6,8}$=2.76 Hz); 6.23 (d, 1H, H$_8$, J$_{8,6}$=2.76 Hz); 4.17 (q, 2H, J=7.11 Hz, CH$_2$CH$_3$); 1.22 (t, 3H, J=7.11 Hz, CH$_3$CH$_2$).

Step 2: Ethyl 7-hydroxy-6-tert-butyl-1, 4-benzodioxin-2-carboxylate

Add 0.425 cm$^3$ (4.5 mmol) of tert-butanol to a solution of 0.5 g (2.25 mmol) of ethyl 7-hydroxy-1,4-benzodioxin-2-carboxylate in 3 cm$^3$ of trifluoroacetic acid. The whole is stirred for 24 hours at room temperature and, after concentrating to dryness under reduced pressure, the crude product is then purified by chromatography on a silica column (eluant:petroleum ether/- diethyl ether 80:20). Ethyl 7-hydroxy-6-tert-butyl-1,4-benzodioxin-2-carboxylate is obtained in a yield of 78%.

Melting point: 222° C.

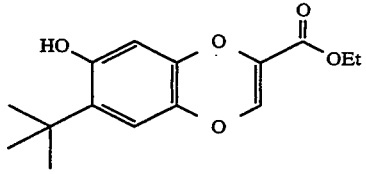

$^1$H NMR (CDCl$_3$), δ (ppm): 6.96 (s, 1H, H$_3$); 6.63 (s, 1H, H$_5$); 6.31 (s, 1H, H$_8$); 5.14 (s, 1H, OH); 4.27 (q, 2H, J=7.3 Hz, CH$_2$CH$_3$); 1.33 (t, 3H, J=7.3 Hz, CH$_3$CH$_2$).

PREPARATION 12: ETHYL 6-HYDROXY-7-TERT-BUTYL-1,4-BENZODIOXIN-2-CARBOXYLATE

By proceeding as for Preparation 11, ethyl 6-hydroxy-7-tert-butyl-1,4-benzodioxin-2-carboxylate is obtained from ethyl 6-acetyl-1,4-benzodioxin-2-carboxylate in a total yield of 63%.

Melting point: 125° C.

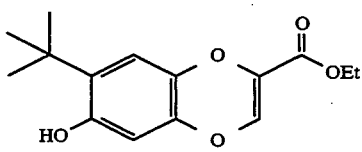

$^1$H NMR (DMSO), δ (ppm): 9.44 (s, 1H, OH); 7.16 (s, 1H, H$_3$); 6.55 (s, 1H, H$_8$); 6.26 (s, 1H, H$_5$); 4.18 (q, 2H, J=7.35 Hz, CH$_2$CH$_3$); 1.26 (s, 9H, (CH$_3$)$_3$C); 1.22 (t, 3H, J=7.35 Hz, CH$_3$CH$_2$).

PREPARATION 13: ETHYL 7-HYDROXY-6-TERT-BUTYL-2,3-DIHYDRO-1,4-BENZODIOXIN-2-CARBOXYLATE

By proceeding as for Preparation 11, ethyl 7-hydroxy-6-tert-butyl-2,3-dihydro-1,4-benzodioxin-2-carboxylate is obtained from ethyl 7-acetoxy-2,3-dihydro-1,4-benzodioxin-2-carboxylate in a total yield of 73%.

Melting point: 128° C.

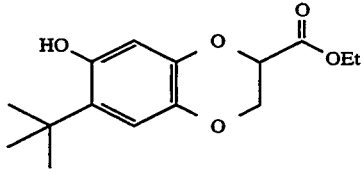

$^1$H NMR (CDCl$_3$), δ (ppm): 6.78 (s, 1H, H$_5$); 6.4 (s, 1H, H$_8$); 4.78 (t, 1H, H$_2$, J=3.68 Hz); 4.66 (s, 1H, OH); 4.33 (d, 2H, H$_{3a}$, H$_{3b}$, J=3.68 Hz); 4.28 (q, 2H, J=7.35 Hz, CH$_2$CH$_3$); 1.36 (s, 9H, (CH$_3$)$_3$C); 1.31 (t, 3H, J=7.35 Hz, CH$_3$CH$_2$).

PREPARATION 14: ETHYL 6-HYDROXY-7-TERT-BUTYL-2,3-DIHYDRO-1,4-BENZODIOXIN-2-CARBOXYLATE

By proceeding as for Preparation 11, ethyl 6-hydroxy-7-tert-butyl-2,3-dihydro-1,4-benzodioxin-2-carboxylate is obtained from ethyl 6-acetoxy-2,3-dihydro-1,4-benzodioxin-2-carboxylate in a total yield of 71%.

Melting point: 172° C.

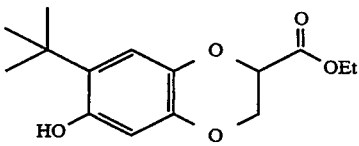

$^1$H NMR (CDCl$_3$), δ (ppm): 6.94 (s, 1H, H$_5$); 6.26 (s, 1H, H$_8$); 4.73–4.71 (m, 1H, H$_2$); 4.52 (s, 1H, OH); 4.4–4.23 (m, 4H, H$_{3a}$, H$_{3b}$, CH$_2$CH$_3$); 1.36 (s, 9H, (CH$_3$)$_3$C); 1.31 (t, 3H, J=7.3 Hz, CH$_3$CH$_2$).

PREPARATION 15: 7-HYDROXY-2,3-DIHYDRO-1,4-BENZODIOXIN-2-CARBOXYLIC ACID

Under a nitrogen atmosphere, slowly add 75 mmol of a 10% aqueous sodium hydroxide solution to a solution of 2 g (7.5 mmol) of ethyl 7-acetoxy-2,3-dihydro-1,4-benzodioxin-2-carboxylate in 20 cm$^3$ of methanol. Stir at room temperature for 6 hours and then, after concentrating under reduced pressure, acidify the mixture with a 2N hydrochloric acid solution. Extract with diethyl ether the acid which precipitates, then, after drying and concentration to dryness, wash the resulting acid with methylene chloride. 7-Hydroxy-2,3-dihydro-1,4-benzodioxin-2-carboxylic acid is thereby obtained in a yield of 85%.

Melting point: 204° C.

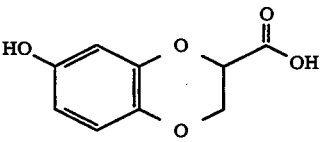

$^1$H NMR (CDCl$_3$), δ (ppm): 4.13 (dd, 1H, H$_{3b}$, J$_{3,2}$=3.55 Hz, J$_{3b,3a}$=11.45 Hz); 4.30 (dd, 1H, H$_{3a}$, J$_{3,2}$=3.55 Hz, J$_{3a,3b}$=11.45 Hz); 4.94 (t, 1H, H$_2$, J$_{2,3}$=3.55 Hz); 6.21 (dd, 1H, H$_6$, J$_{6,5}$=8.29 Hz, J$_{6,8}$=2.76 Hz); 6.3 (d, 1H, H$_8$, J$_{8,6}$=2.76 Hz); 6.61 (d, 1H, H$_5$, J$_{5,6}$=8.29 Hz); 9 (s, 1H, OH); 13.22 ( s broad, 1H, COOH).

PREPARATIONS 16 TO 23

By proceeding as for Preparation 15, but replacing ethyl 7-acetoxy-2,3-dihydro-1,4-benzodioxin-2-carboxylate with:

ethyl 6-acetoxy-2,3-dihydro-1,4-benzodioxin-2-carboxylate, 6-hydroxy-2,3-dihydro-1,4-benzodioxin-2-carboxylic acid is obtained in a yield of 90%.

Melting point: 165° C.

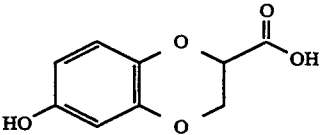

$^1$H NMR (DMSO) δ (ppm): 13 (s broad, 1H, COOH); 9 (s, 1H, OH), 6.69 (d, 1H, H$_8$, J$_{8,7}$=7.58 Hz); 6.31–6.19 (m, 2H, H$_5$, H$_7$); 4.88 (t, 1H, H$_2$, J$_{2,3}$=3.79 Hz); 4.36–4.18 (m, 2H, H$_{3a}$, H$_{3b}$).

ethyl 7-acetoxy-1,4-benzodioxin-2-carboxylate, 7-hydroxy-1,4-benzodioxin-2-carboxylic acid is obtained in a yield of 88%.

Melting point: 280° C.

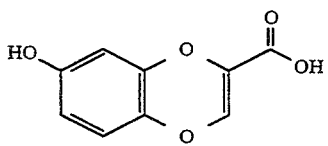

¹H NMR (DMSO), δ (ppm): 6.21 (d, 1H, H₈, J₈,₆=2.84 Hz); 6.28 (dd, 1H, H₆, J₆,₅=8.53 Hz, J₆,₈=2.84 Hz); 6.65 (d, 1H, H₅, J₅,₆=8.53 Hz); 7.14 (s, 1H, H₃); 9.5 (s, 1H), OH); 13 (s broad, 1H, COOH).

ethyl 6-acetoxy-1,4-benzodioxin-2-carboxylate, 6-hydroxy-1,4-benzodioxin-2-carboxylic acid is obtained in a yield of 87%.
Melting point: 260° C.

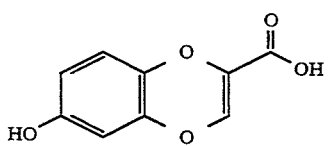

¹H NMR DMSO), δ (ppm): 13 (s broad, 1H, COOH); 9.44 (s, 1H, OH); 7.11 (s, 1H, H₃); 6.66 (d, 1H, H₈, J₈,₇=8.29 Hz); 6.33 (dd, 1H, H₇, J₇,₈=8.29 Hz, J₇,₅=1.97 Hz); 6.24 (d, 1H, H₅, J₅,₇=1.97 Hz).

ethyl 7-acetoxy-6-tert-butyl-1,4-benzodioxin-2-carboxylate. 7-hydroxy-6-tert-butyl-1,4-benzodioxin-2-carboxylic acid is obtained.
Melting point: 144° C.

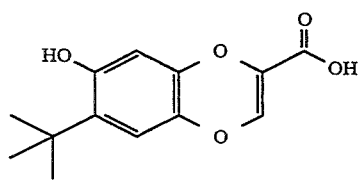

¹H NMR (DMSO); δ (ppm): 12.96 (s broad, 1H, COOH); 9.44 (s, 1H, OH); 7.13 (s, 1H, H₃); 6.53 (s, 1H, H₅); 6.25 (s, 1H, H₈); 1.27 (s, 9H, (CH₃)₃C).

ethyl 7-acetoxy-6-tert-butyl-2,3-dihydro-1,4-benzodioxin-2-carboxylate, 7-hydroxy-6-tert-butyl -2,3-dihydro-1,4-benzodioxin-2-carboxylic acid is obtained.
Melting point: 264° C.

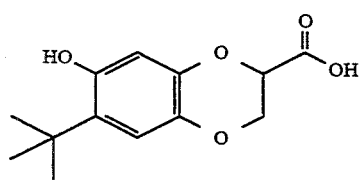

¹NMR (DMSO), δ (ppm): 13 (s, 1H, COOH); 8.88 (s, 1H, OH); 6.51 (s, 1H, H₈); 6.34 (s, 1H, H₅); 4.6–4.4 (m, 1H, H₂); 4.24.0 (m, 2H, H₃ₐ, H₃b); 1.21 (s, 9H, (CH₃)₃C).

ethyl 6-acetoxy-7-tert-butyl-1,4-benzodioxin-2-carboxylate, 6-hydroxy-7-tert-butyl-1,4-benzodioxin-2-carboxylic acid is obtained.
Melting point: 130° C.

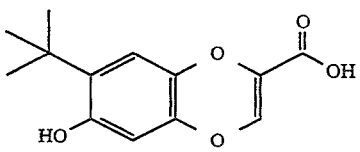

¹H NMR (DMSO), δ (ppm): 13 (s broad, 1H, COOH); 9.4 (s, 1H, OH); 7.09 (s, 1H, H₃); 6.55 (s, 1H, H₈); 6.26 (s, 1H, H₅); 1.28 (s, 9H, (CH₃)₃C).

ethyl 6-acetoxy-7-tert-butyl-2,3-dihydro-1,4-benzodioxin-2-carboxylate, 6-hydroxy-7-tert-butyl-2,3-dihydro-1,4-benzodioxin-2-carboxylic acid is obtained.
Melting point: 162° C.

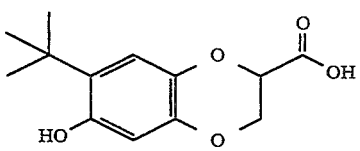

¹H NMR (DMSO), δ (ppm): 13.2 (s broad, 1H, COOH); 8.91 (s, 1H, OH); 6.65 (s, 1H, H₈); 6.31 (s, 1H, H₅); 4.88 (t, 1H, H₂, J₂,₃=2.94 Hz); 4.33–4.17 (m, 2H, H₃ₐ, H₃b); 1.27 (s, 9H, (CH₃)₃C).

ethyl 1,4-benzodioxin-2-carboxylate, 1,4-benzodioxin-2-carboxylic acid is obtained in a yield of 95%.
Melting point: 180° C.

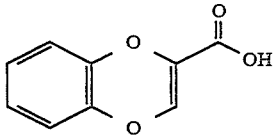

PREPARATION 24: 6-METHOXY-1,4-BENZODIOXIN-2-CARBOXYLIC ACID

Step 1: Methyl 6-hydroxy-1,4-benzodioxin-2-carboxylate

Add 3.8 mmol of a 2M solution of sodium methanolate to a solution of 0.38 mmol of ethyl 6-acetoxy -1,4-benzodioxin-2-carboxylate in 5 cm³ of anhydrous methanol. After stirring for 4 hours at room temperature and neutralising with acid Dowex resin, the reaction mixture is concentrated under reduced pressure and the crude product obtained is purified by chromatography on a silica column (eluant:petroleum ether/diethyl ether, 80:20). Methyl 6-hydroxy -1,4-benzodioxin-2-carboxylate is thereby obtained in a yield of 87%.

Step 2: Methyl 6-methoxy-1,4-benzodioxin-2-carboxylate

Stir for 15 minutes at room temperature, under argon, a solution of 0.48 mmol of methyl 6-hydroxy -1,4-benzodioxin-2-carboxylate in 5 cm³ of N,N-dimethylformamide in the presence of 0.57 mmol of 60% sodium hydride suspended in oil, and then add 0.72 mmol of methyl iodide. After being stirred for 4 hours at room temperature, the reaction mixture is concentrated under reduced pressure and then extracted with methylene chloride. After the methylene chloride phases have been concentrated to dryness, the crude product is purified by chromatography on a silica column (eluant:petroleum ether/ethyl acetate, 80:20). Methyl 6-methoxy-1,4-benzodioxin-2-carboxylate is thereby obtained in a yield of 78%.

Step 3: 6-Methoxy-1,4-benzodioxin-2-carboxylic acid

That compound is obtained in accordance with Preparation 15 in a yield of 95%, starting from methyl 6-methoxy-1,4-benzodioxin-2-carboxylate.

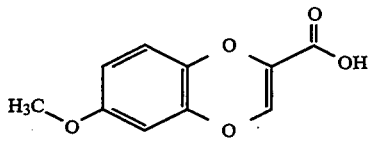

$^1$H NMR (DIMSO), δ (ppm): 13.2 (s broad, 1H, COOH); 7.16 (s, 1H, H$_3$); 6.78 (d, 1H, H$_8$, J$_{8,7}$=8.9 Hz); 6.55–6.45 (m, 2H, H$_7$, H$_5$); 3.68 (s, 3H, CH$_3$O).

EXAMPLE 1

6-HYDROXY-2-{4-[BIS(4-FLUOROPHENYL)METHYL]PIPERAZIN-1-YLCARBONYL}-1,4-BENZODIOXIN

Under a nitrogen atmosphere, add 5.5 mmol of 1-[bis(4-fluorophenyl)methyl]piperazine, 5.5 mmol of EDCI (1-(3-dimethylaminopropyl)-3-ethylcarbodiimide) and 5.5 mmol of HOBt (hydroxybenzotriazole) in succession to a solution at 0° C. of 5 nmml of 6-hydroxy-1,4-benzodioxin-2-carboxylic acid in 25 cm$^3$ of N,N-dimethylformamide. Stir for 2 hours at 0° C. and then for 12 hours at room temperature, and concentrate the reaction mixture under reduced pressure. Extract the resulting amide with diethyl ether and then, after concentration to dryness, purify the crude product by chromatography on a silica column (eluant:petroleum ether then an increasing gradient of ethyl acetate in petroleum ether). 6-Hydroxy-2-{4-[bis-(4-fluorophenyl)methyl]piperazin-1-ylcarbonyl}-1,4-benzodioxin is thereby obtained in a yield of 85%. The product obtained is precipitated from 10 ml of pentane and is then filtered and recrystallised from cyclohexane.

Melting point: 163° C.

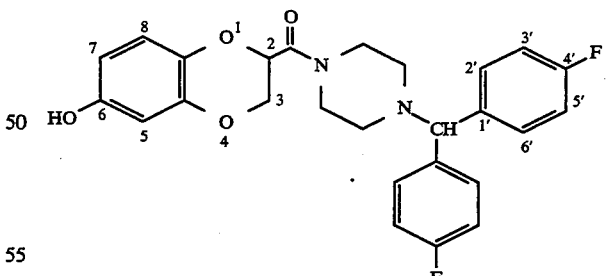

$^1$H NMR (CDCl$_3$), δ (ppm): 7.34 (dd, 4H, 2×H$_{2'}$, H$_{6'}$, J$_{2',3'}$=8.6 Hz, J$_{3',F}$=5.53 Hz); 6.98 (t, 4H, 2×H$_{3+}$, H$_{5'}$, J$_{3',2'}$=J$_{3'F}$=8.69 Hz); 6.57 (s, 1H, H$_3$); 6.48 (d, 1H, H$_8$, J$_{8,7}$=8.69 Hz); 6.29 (dd, 1H, H$_7$, J$_{7,8}$=8.69 Hz, J$_{7,5}$=3.16 Hz); 6.23 (d, 1H, H$_5$, J$_{5,7}$=3.16 Hz); 5.6 (s, 1H, OH); 4.25 (s, 1H, NCHAr); 3.65–3.4 (m, 4H$_{piperazine}$); 2.39–2.29 (m, 4H$_{piperazine}$). IR(KBr)ν(cm-1): 3610–2980 (OH), 1665 (C=O), 1210 (C—O—C).

That compound can also be obtained by replacing HOBt with DMAP (4-dimethylaminopyridine).

By proceeding in the same manner but varying the amines and the acids, the following compounds are obtained.

EXAMPLE 2

7-HYDROXY-2-{4-[BIS(4-FLUOROPHENYL)METHYL]PIPERAZIN-1-YLCARBONYL}-1,4-BENZODIOXIN

That compound is obtained in a yield of 76% starting from 1-[bis(4-fluorophenyl)methyl]piperazine and 7-hydroxy-1,4-benzodioxin-2-carboxylic acid.

Melting point: 221 ° C.

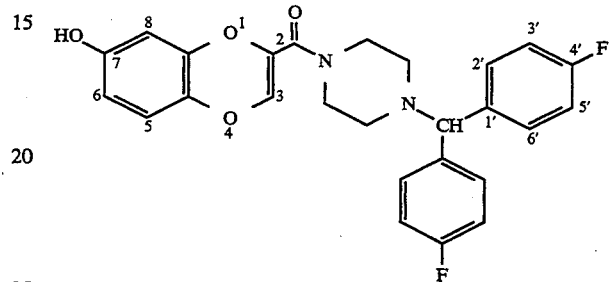

$^1$H NMR (CDCl$_3$), δ (ppm): 7.36 (dd, 4H, 2×H$_{2'}$, H$_{6'}$, J$_{2',3'}$=8.75 Hz, J$_{2',F}$=5.63 Hz); 7 (t, 4H, 2×H$_{3'}$, H$_{5'}$, J$_{3',2'}$=8.75 Hz, J$_{3',F}$=8.75 Hz); 6.58–6.52 (m, 2H, H$_3$, H$_5$); 6.29 (dd, 1H, H$_6$, J$_{6,5}$=8.13 Hz, J$_{6,8}$=2.5 Hz); 6.23 (s, 1H, H$_8$, J$_{8,6}$=2.5 Hz); 5.4 (s, 1H, OH); 4.27 (s, 1H, N—CH—Ar); 3.69–3.63 (m, 4H$_{piperazine}$); 2.45–2.39 (m, 4H$_{piperazine}$). IR(KBr)ν(cm-1): 3610–3180–2900 (OH), 1650 (C=O), 1210 (=C—O—C).

EXAMPLE 3

6-HYDROXY-2-{4-[BIS(4-FLUOROPHENYL)METHYL]PIPERAZIN-1-YLCARBONYL}-2,3-DIHYDRO-1,4-BENZODIOXIN

That compound is obtained a yield of 80% starting from 1-[bis(4-fluorophenyl)methyl]piperazine and 6-hydroxy-2,3-dihydro-1,4-benzodioxin-2-carboxylic acid.

Melting point: 201 ° C.

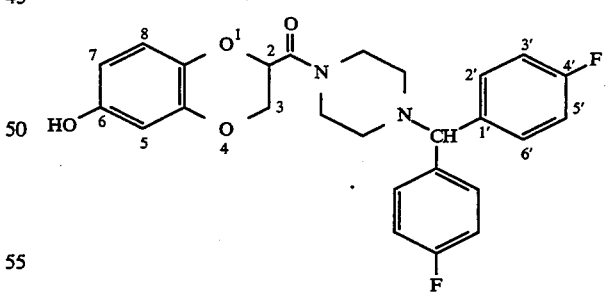

$^1$H NMR (CDCl$_3$), δ (ppm): 7.4–7.3 (m, 4H, 2×H$_{2'}$, H$_{6'}$); 7 (t split, 4H, 2×H$_{3'}$, H$_{5'}$, J$_{3',2'}$=J$_{3',F}$=8.69 Hz), 6.71 (d, 1H, H$_8$, J$_{8,7}$=8.69 Hz); 6.4 (d, 1H, H$_5$, J$_{5,7}$=3.16 Hz); 6.23 (dd, 1H, H$_7$, J$_{7,5}$=3.16 Hz, J$_{7,8}$=8.69 Hz); 4.92 (s, 1H, OH); 4.92 (s, 1H, OH); 4.72 (dd, 1H, H$_2$, J$_1$=2.37 Hz, J$_2$=7.9 Hz); 4.43 (dd, 1H, H$_{3a}$, J$_1$=2.37 Hz, J$_2$=11.85 Hz); 4.29 (dd, 1H, H$_{3b}$, J$_1$=5.9 Hz, J$_2$=11.85 Hz); 4.27 (s, 1H, N—CH—Ar); 3.82–3.2 (m, 4H$_{piperazine}$); 2.5–2.32 (m, 4H$_{piperazine}$). IR(KBr)ν(cm-1): 3680–3000 (OH), 1630 (C=O), 1485 (C=C), 1210-1140-1085 (C—O—C).

EXAMPLE 4

7-HYDROXY-2-{4-[BIS(4-FLUOROPHENYL)ME-THYL]PIPERAZIN-1-YL CARBONYL}-2,3-DIHYDRO-1,4-BENZODIOXIN

That compound is obtained in a yield of 65% starting from 1-[bis(4-fluorophenyl)methyl]piperazine and 7-hydroxy-2,3-dihydro-1,4-benzodioxin-2-carboxylic acid.

Melting point: 136° C.

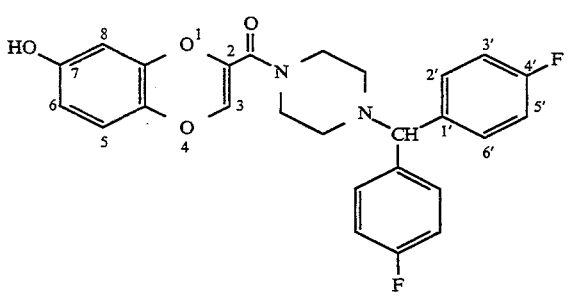

$^1$H NMR (CDCl$_3$), δ (ppm): 7.43–7.31 (m, 4H, 2×H$_{2'}$, H$_{6'}$); 7.04–6.98 (m, 4H, 2×H$_{3'}$, H$_{5'}$); 6.73 (d, 1H, H$_5$, J$_{5,6}$=8.2 Hz); 6.43 (d, 1H, H$_8$, J$_{8,6}$=2.71 Hz); 6.34 (dd, 1H, H$_6$, J$_{6,8}$=2.71 Hz, J$_{6,5}$=8.2 Hz); 5.2 (s broad, 1H, OH); 4.81 (dd, 1H, H$_2$, J$_{2,3b}$=2.53 Hz, J$_{2,3a}$=3.05 Hz); 4.37 (dd, 1H, H$_{3a}$, J$_{3a,2}$=3.05 Hz, J$_{3a,3b}$=6.32 Hz); 4.3–4.16 (m, 2H, CH—Ar, H$_{3b}$); 3.8–3.5 (m, 4H$_{piperazine}$); 2.53–2.29 (m, 4H$_{piperazine}$). IR(KBr)υ(cm-1): 3600-3300-3000 (OH), 1640 (C=O), 1220–1150 (C—O—C).

EXAMPLE 5

7-HYDROXY-6-TERT-BUTYL-2-{4-[BIS-(4-FLUOROPHENYL) METHYL]PIPERAZIN-1-YLCARBONYL}-2,3-DIHYDRO-1,4-BENZODIOXIN

That compound is obtained in a yield of 72% starting from 1-[bis(4-fluorophenyl)methyl]piperazine and 7-hydroxy-6-tert-butyl-2,3-dihydro-1,4-benzodioxin-2-carboxylic acid.

Melting point: 165° C.

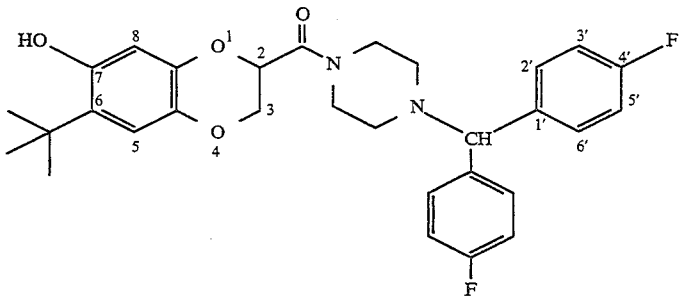

$^1$H NMR (DMSO), δ (ppm): 8.9 (s, 1H, OH); 7.45 (dd, 4H, 2×H$_{2'}$, H$_{6'}$, J$_{2',3'}$=8.08 Hz, J$_{2',F}$=5.89 Hz); 7.14 (t, 4H, 2×H$_{3'}$, H$_{5'}$, J$_{3',2'}$=J$_{3',F}$=8.08 Hz); 6.55 (s, 1H, H$_5$); 6.3 (s, 1H, H$_8$); 5.04 (dd, 1H, H$_2$, J$_2$=2.21 Hz, J$_1$=6.62 Hz); 4.45 (s, 1H, N—CH—Ar); 4.22 (dd, 1H, H$_{3a}$, J$_2$=2.21 Hz, J$_1$=11.76 Hz); 4.02 (dd, 1H, H$_{3b}$, J$_1$=11.76 Hz, J$_2$=6.62 Hz); 3.66–3.34 (m, 4H$_{piperazine}$); 2.42–2.18 (m, 4H$_{piperazine}$); 127 (s, 9H, (CH$_3$)$_3$C). IR(KBr)υ(cm-1): 3640–3060 (OH), 1635 (C=O), 1495 (C=C), 1170–1070 (C—O—C).

EXAMPLE 6

7-HYDROXY-6-TERT-BUTYL-2-{4-[BIS-(4-FLUOROPHENYL) METHYL]PIPERAZIN-1-YLCARBONYL}-1,4-BENZODIOXIN

That compound is obtained in a yield of 72% starting from 1-[bis(4-fluorophenyl)methyl]piperazine and 7-hydroxy-6-tert-butyl-1,4-benzodioxin-2-carboxylic acid.

Melting point: 184° C.

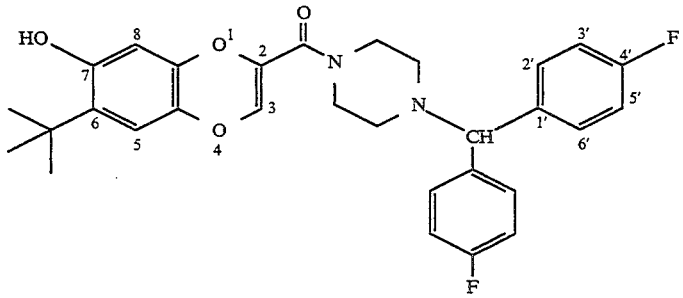

$^1$H NMR (DMSO), δ (ppm): 7.34 (dd, 4H, 2×H$_{2'}$, H$_{6'}$, J$_{2',3'}$=8.22 Hz, J$_{2',F}$=5.05 Hz); 7 (t, 4H, 2×H$_{3'}$, H$_{5'}$, J$_{3',2'}$=J$_{3',F}$=8.22 Hz); 6.74 (s broad, 1H, OH); 6.56 (s, 1H, H$_3$); 6.45 (s, 1H, HS); 6.24 (s, 1H, H$_8$); 4.23 (s, 1H, NCHAr); 3.8–3.6 (m, 4H$_{piperazine}$); 2.6–2.2 (m, 4H piperazine); 1.42 (s, 9H, (CH$_3$)$_3$C). IR(KBr)υ(cm-1): 3680–3210–3000 (OH), 1660 (C=O), 1600–1485 (C=C), 1290–1220 (=C—O—C).

EXAMPLE 7

6-HYDROXY-7-TERT-BUTYL-2-{4-[BIS-(4-FLUOROPHENYL) METHYL]PIPERAZIN-1-YLCARBONYL}-2,3-DIHYDRO-1,4-BENZODIOXIN

That compound is obtained in a yield of 74% starting from 1-[bis(4-fluorophenyl) methyl]piperazine and 6-hydroxy-7-tert-butyl-2,3-dihydro-1,4-benzodioxin-2-carboxylic acid.

Melting point: 174° C.

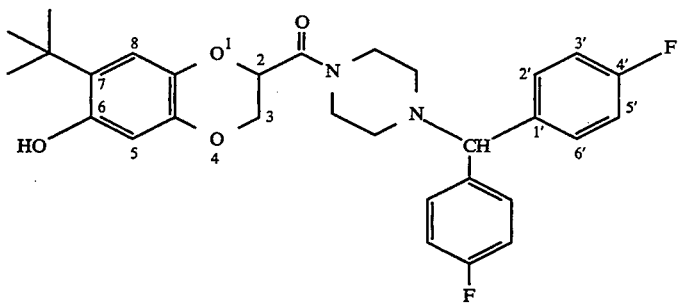

¹H NMR (DMSO), δ (ppm): 8.91 (s, 1H, OH); 7.45 (dd, 4H, 2×H₆', H₂', J₂',₃'=8.82 Hz, J₂',F=5.88 Hz); 7.14 (t, 4H, H₃', H₅', J₃',₂'=J₃',F=8.82 Hz); 6.57 (s, 1H H₈); 6.27 (s, 1H, H₅); 4.97 (dd, 1H, H₂, J₁=2.2 Hz, J₂=7.4 Hz); 4.45 (s, 1H, NCHAr); 4.26 (dd, 1H, H₃ₐ, J₁=2,2 Hz, J₂=11.8 Hz); 4.02 (dd, 1H, H₃ᵦ, J₂=11.8 Hz, J₁=7.4 Hz); 3.54–3.44 (m, 4H*piperazine*); 2.4–2.2 (m, 4H*piperazine*); 1.26 (s, 9H, (CH₃)₃C). IR(KBr)ʋ(cm-1): 3640–3000 (OH), 1630 (C=O), 1495 (C=C), 1220–1175 (C—OC).

EXAMPLE 8

6-HYDROXY-7-TERT-BUTYL-2-{4-[BIS-(4-FLUOROPHENYL) METHYL ]PIPERAZIN-1-YLCARBONYL}-1,4-BENZODIOXIN

That compound is obtained in a yield of 83% starting from 1-[bis-(4-fluorophenyl)methyl]piperazine and 6-hydroxy-7-tert-butyl-1,4-benzodioxin-2-carboxylic acid.

Melting point: 242° C.

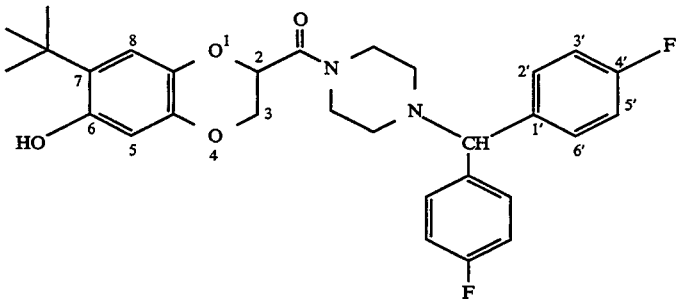

¹H NMR (DMSO), δ (ppm): 9.36 (s, 1H, OH); 7.43 (dd, 4H2×H₂', H₆', J₂',₃'=8.32 Hz, J₂',F=5.88 Hz); 7.12 (t, 4H, 2×H₃', H₅', J₃',₂'=J₃',F=8.35 Hz); 6.64 (s, 1H, H₃); 6.52 (s, 1H, H₈); 6.24 (s, 1H, H₅); 4.44 (s, 1H, NCHAr); 3.60–3.46 (m, 4H*piperazin*); 2.5–2.1 (m, 4H*piperazine*); 1.25 (s, 9H (CH₃)₃C). IR(KBr)ʋ(cm-1): 3680–3010 (OH), 1670 (C=O), 1600–1500 (C=C), 1220–1180 (=C—O—C).

EXAMPLE 9

2-{4-[BIS-(4-FLUOROPHENYL)METHYL]PIPERAZIN-1-YL CARBONYL}-1,4-BENZODIOXIN

That compound is obtained in a yield of 78% starting from 1-[bis(4-fluorophenyl)methyl]piperazine and 1,4-benzodioxin-2-carboxylic acid.

Melting point: 156° C.

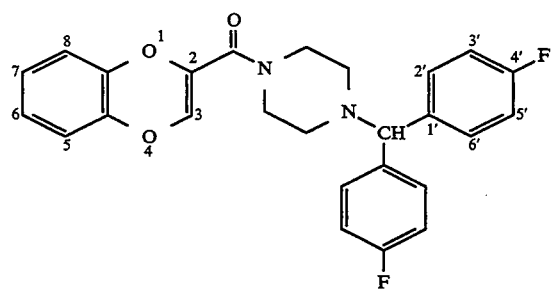

¹H NMR (DMSO), δ (ppm): 7.43 (dd, 4H, 2×H₂', H₆', J₂',₃=8.8 Hz, J₂',F=5.15 Hz); 7.12 (t, 4H, 2×H₃', H₅', J₃',₂'=J₃',F=8.8 Hz); 6.92–6.78 (m, 4H*aromatic*); 6.74 (s, 1H, H₃); 4.43 (s, 1H, N—CH—Ar); 3.7–3.4 (m, 4H *piperazine*); 2.3–2.15 (m, 4H*piperazine*). IR(KBr)ʋ(cm-1): 3610–3100–3000 (OH), 2980–2780 (CH₂, CH₃), 1690 (C=C), 1670 (C=O), 1620–1595 (C=C), 1240–1220–1150–1100 (=C—O—C).

EXAMPLE 10

6-HYDROXY-2-ANILINOCARBONYL-1,4-BENZODIOXIN

That compound is obtained in a yield of 72% starting from aniline and 6-hydroxy-1.4-benzodioxin-2-carboxylic acid.

Melting point: 210° C.

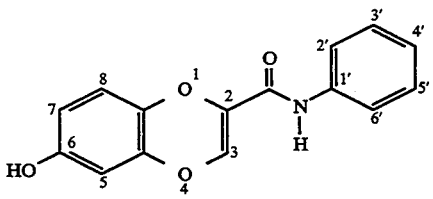

$^1$H NMR (DMSO), δ (ppm): 9.5 (s, 1H, OH); 7.68 (d, 2H, 2×H$_{2'}$, H$_{6'}$, J$_{2',3'}$=7.9 Hz); 7.32 (t, 2H, H$_{3'}$, H$_{5'}$, J=7.9 Hz); 7.09 (t, 1H, H$_{4'}$, J=7.9 Hz); 7.07 (s, 1H, H$_3$); 6.78 (d, 1H, H$_8$, J$_{8,7}$=8.69 Hz); 6.37 (dd, 1H, H$_7$, J$_{7,8}$=8.69 Hz, J$_{7,5}$=3.16 Hz); 6.27 (d, 1H, H$_5$, J$_{5,7}$=3.16 Hz); 4.64 (s, 1H, NH). IR(KBr)υ(cm-1): 3610–3000 (OH), 3380 (NH), 1675 (C=O), 1635 (C=C), 1325 (C—O), 1220–1180–1085 (=C—O—C).

EXAMPLE 11

6-HYDROXY-2-ANILINOCARBONYL-2,3-DIHYDRO-1,4-BENZODIOXIN

That compound is obtained in a yield of 75% starting frown aniline and 6-hydroxy-2,3-dihydro -1,4-benzodioxin-2-carboxylic acid.

Melting point: 147° C.

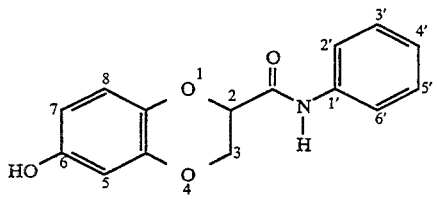

$^1$H NMR (DMSO), δ(ppm): 10 (s, 1H, NH); 9.02 (s, 1H, OH); 7.62 (d, 2H, H$_{2'}$, H$_{6'}$, J=7.58); 7.30 (t, 2H, H$_{3'}$, H$_{5'}$, J=7.58 Hz); 7.07 (t, 1H, H$_{4'}$, J=7.1 Hz); 6.81 (d, 1H, H$_8$, J$_{8,7}$=8.29 Hz); 6.29–6.27 (m, 2H, H$_7$, H$_5$); 4.81 (dd, 1H, H$_2$, J$_1$=2.76 Hz, J$_2$=6.32 Hz); 4.78 (dd, 1H, H$_{3a}$, J$_1$=2.76 Hz, J$_2$=11.45 Hz); 4.50 (dd. 1H, H$_{3b}$, J$_1$=11.45 Hz, J$_2$=6.32 Hz). IR(KBr)υ(cm-1): 3610-3100(OH),3370(NH), 1665(C=O), 1310-1185-1145-(C—O—C).

EXAMPLE 12

7-HYDROXY-2-ANILINOCARBONYL-2,3-DIHYDRO-1,4-BENZOP DIOXIN

That compound is obtained in a yield of 65% starting from aniline and 6-hydroxy-2,3-dihydro-1,4-benzodioxin-2-carboxylic acid.

Melting point: 158° C.

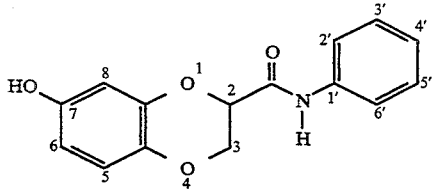

$^1$H (CDCl$_3$), δ (ppm): 8.33 (s, 1H, NH); 7.56 (d, 2H, H$_{2'}$, H$_{6'}$, J=7.6 Hz); 7.35 (t, 2H, H$_{3'}$, H$_{5'}$, J=7.6 Hz); 7.16 (t, 1H, H$_{4'}$, J=7.6 Hz); 6.79 (d, 1H, H$_{5,6}$=8.8 Hz); 6.57 (d, 1H, H$_8$, J$_{8,6}$=3.1 Hz); 6.41 (dd, 1H, H$_6$, J$_{6,5}$=8.8 Hz, J$_{6,8}$=3.1 Hz); 5.1 (s, 1H, OH); 4.79 (1H, H$_2$, J$_1$=7.11 Hz, J$_2$=3.16 Hz); 4.54 (dd, 1H, H$_{3a}$, J$_1$=11.9 Hz, J$_2$=3.16 Hz); 4.24(dd, 1H, H$_{3b}$, J$_1$=11.9 Hz, J$_2$=7.11Hz). IR(KBr)υ(cm-1): 3500-3000 (OH, NH), 3310 (NH$_{associated}$), 1635 (C=O), 1100-1030 (C—O—C).

EXAMPLE 13

7-HYDROXY-2-ANILINOCARBONYL-1,4-BENZODIOXIN

That compound is obtained in a yield of 63% starting from aniline and 7-hydroxy-1,4-benzodioxin-2-carboxylic acid.

Melting point: 206° C.

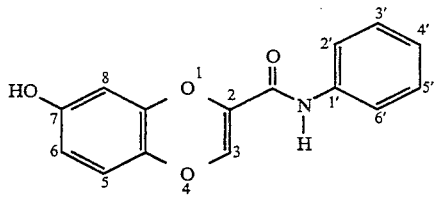

1H NMR (CDCl$_3$), δ (ppm): 7.83 (s, 1H, NH); 7.59 (d, 2H, H$_{2'}$, H$_{6'}$, J=7.9 Hz); 7.36 (t, 2H, H$_{3'}$, H$_{5'}$, J=7.9 Hz); 7.16 (t, 1H, H$_{4'}$); 6.64 (d, 1H, H$_5$, J$_{5,6}$=8.3 Hz); 6.38 (d, 1H, H$_8$, J$_{8,6}$=2.8 Hz); 6.36 (dd, 1H, H$_6$, J$_{6,8}$=2.8 Hz, J$_{6,5}$=2.3 Hz); 4.95 (s, 1H, OH). IR(KBr)υ(cm-1): 3500-2980 (NH, OH), 3310 (NH$_{associated}$), 1640 (C=O), 1220-1070 (C—O—C).

EXAMPLE 14

6-HYDROXY-2-(N-BUTYLANILINOCARBONYL)-I,4-BENZODIOXIN

That compound is obtained in a yield of 91% starting from N-butylaniline and 6-hydroxy-1,4-benzodioxin-2-carboxylic acid.

Melting point: 124° C.

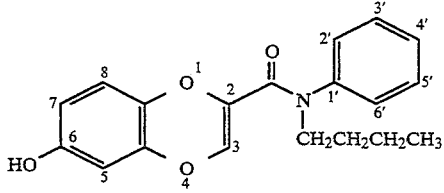

$^1$H NMR (CDCl$_3$), δ (ppm): 7.4-7.18 (m, 5H$_{aromatic}$, N—Ar); 6.62 (s, 1H, H$_3$); 6.14 (d, 1H, H$_5$, J$_{5,7}$=2.9 Hz); 6 (dd, 1H, H$_7$, J$_{7,8}$=8.3 Hz, J$_{7,5}$=2.9 Hz); 5.71 (d, 1H, H$_8$, J$_{8,7}$=8.3 Hz); 5.14 (s, 1H, OH); 3.9-3.7 (m, 2H, NCH$_2$CH$_2$); 1.56-1.47 (m, 2H, CH$_2$CH$_2$CH$_3$); 1.5-1.2 (m, 2H, CH$_2$CH$_3$); 0.88 (t, 3H, J=7.3 Hz, CH$_2$CH$_3$). IR(KBr)υ(cm-1): 3610-2980 (OH), 3310 (NH), 1660 (C=O), 1595-1575-1490 (C=C), 1290-175-1130-1090 (=C—O—C).

EXAMPLE 15

7-HYDROXY-2-(N-BUTYLANILINOCARBONYL)-I,4-BENZODIOXIN

That compound is obtained in a yield of 78% starting from N-butylaniline and 7-hydroxy-1,4-benzodioxin-2-carboxylic acid.

Melting point: 156° C.

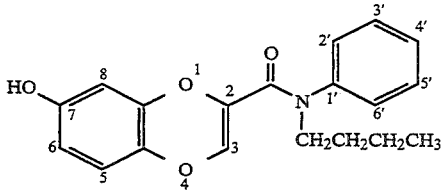

$^1$H NMR (CDCl$_3$), δ (ppm): 7.43-7.17 (m, 5H$_{aromatic}$); 6.6 (d, 1H, H$_8$, J$_{8,6}$=2.9 Hz); 6.44 (d, 1H, H$_5$, J$_{5,6}$=8.7 Hz); 6.42 (s, 1H, H$_3$); 6.20 (dd, 1H, H$_8$, J$_{8,6}$=2.9 Hz); 8.7

Hz); 5.56 (s, 1H, OH); 3.76 (t, 2H, NCH$_2$CH$_2$, J=7.8 Hz); 1.7–1.48 (m, 2H, NCH$_2$CH$_2$CH$_2$); 1.43–1.26 (m, 2H, NCH$_2$CH$_2$CH$_2$CH$_3$); 0.89 (t, 3H, J=7.31 Hz, CH$_2$CH$_3$). IR(KBr)υ(cm-1): 3610–2980 (OH), 3210 (NH), 1660 (C=O), 1590–1570–1485 (C=C), 1220–1155–1070 (=C—O—C).

EXAMPLE 16

7-HYDROXY-2-[4-(2,3,4-TRIMETHOXYBENZYL)-PIPERAZIN-1-YLCARBONYL]-1,4-BENZODIOXIN

That compound is obtained in a yield of 73% starting from 1-(2,3,4-trimethoxybenzyl)piperazine and 7-hydroxy-1,4-benzodioxin-2-carboxylic acid.

Melting point: 93° C.

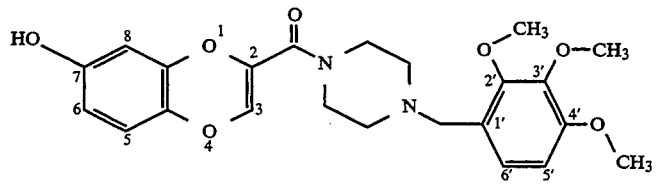

$^1$H NMR (CDCl$_3$), δ (ppm): 2.55–2.46 (m, 4H$_{piperazine}$); 3.51 (s, 2H, N—CH$_2$—Ar); 3.68–3.6 (m, 4H$_{piperazine}$); 3.87–3.89 (3s, 9H, 333 CH$_3$O); 6.25 (d, 1H, H$_8$, J$_{8,6}$=2.08 Hz); 6.31 (dd, 1H, H$_6$, J$_{6,8}$=2.08 Hz, J$_{6,5}$8.33 Hz); 6.53 (d, 1H, H$_5$, J$_{5,6}$=8.33 Hz); 6.54 (s, 1H, H$_3$); 6.63 (d, 1H, J$_{1',2'}$=8.3 Hz); 6.97 (d, 1H, J$_{2',1'}$=8.3 Hz). IR(KBr)υ(cm-1): 3610–3010 (OH), 2980 (ArOCH$_3$), 1640 (C=O), 1250–1080 (=C—O—).

EXAMPLE 17

7-HYDROXY-2-[4-(2,3,4-TRIMETHOXYBENZYL)-PIPERAZIN-1-YLCARBONYL]-2,3-DIHYDRO-1,4-BENZODIOXIN

That compound is obtained in a yield of 65% starting from 1-(2,3,4-trimethoxy benzyl)piperazine and 7-hydroxy-2,3-dihydro-1,4-benzodioxin-2-carboxylic acid.

Melting point: 88° C.

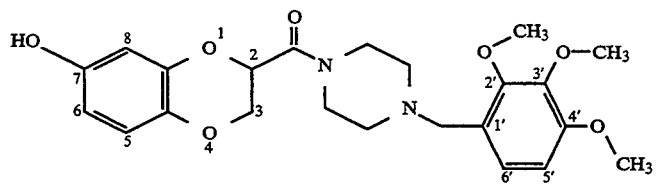

$^1$H NMR (CDCl$_3$), δ (ppm): 2.42–2.52 (m, 4H$_{piperazine}$); 3.54 (s, 2H, N—CH$_2$—Ar); 3.52–3.78 (m, 4H$_{piperazine}$); 3.69–3.87–3.89 (3s, 9H, CH$_3$O); 4.21 (dd, 1H, H$_{3b}$, J$_2$=11.44 Hz, J$_1$=8.32 Hz); 4.4 (dd, 1H, H$_{3a}$, J$_1$=2.08 Hz, J$_{3',3}$=11.4 Hz); 4.82 (dd, 1H, H$_2$, J$_2$=8.32 Hz, J$_1$=2.08 Hz); 6.33 (dd, 1H, H$_6$, J$_{6,8}$=2.5 Hz, J$_{6,5}$=8.12 Hz); 6.44 (d, 1H, H$_8$, J$_{8,6}$=2.5 Hz); 6.64 (d, 1H, H$_5$, J$_{5,6}$=8.12 Hz); 6.74 (d, 1H, H$_{5'}$, J=8.5 Hz); 6.97 (d, 1H, H$_{6'}$, J=8.5 Hz). IR(KBr)υ(cm-1): 3610–3000 (OH), 1660 (C=O), 1590 (C=C), 1150–1080 (C—O—C).

EXAMPLES 18 TO 48

The following are obtained by proceeding in the same manner:

EXAMPLE 18

6-Hydroxy-7-tert-butyl-2-piperidinocarbonyl-1,4-benzodioxin

EXAMPLE 19

6-Hydroxy-7-tert-butyl-2-hexamethyleneiminocarbonyl-1,4-benzodioxin

EXAMPLE 20

6-Hydroxy-7-tert-butyl-2-pyrrolidinocarbonyl-1,4-benzodioxin

EXAMPLE 21

6-Hydroxy-2-(4-phenylpiperidinocarbonyl)-1,4-benzodioxin

EXAMPLE 22

6-Hydroxy-2-(4-benzylpiperidinocarbonyl)-1,4-benzodioxin

EXAMPLE 23

6-Hydroxy-2-(4-methylpiperidinocarbonyl)-1,4-benzodioxin

EXAMPLE 24

6-Hydroxy-2-[4-(4-fluorobenzoyl)piperidinocarbonyl]-1,4-benzodioxin

EXAMPLE 25

6-Hydroxy-2-{4-[bis-(4-fluorophenyl)methylene]-piperidinocarbonyl}-1,4-benzodioxin

EXAMPLE 26

2-{4-[Bis-(4-fluorophenyl)methyl]piperidinocarbonyl}-1,4-benzodioxin

EXAMPLE 27

6-Hydroxy-2-[N-(n-but-1-yl)aminocarbonyl]-1,4-benzodioxin

EXAMPLE 28

6-Hydroxy-2-(N,N-dipropylaminocarbonyl)-1,4-benzodioxin

EXAMPLE 29

6-Hydroxy-7-tert-butyl-2-(N-methylanilinocarbonyl)-1,4-benzodioxin

EXAMPLE 30
6-Hydroxy-7-tert-butyl-2-(N-butylanilinocarbonyl)-1,4-benzodioxin

EXAMPLE 31
6-Hydroxy-2-(3-methoxyanilinocarbonyl)-1,4-benzodioxin

EXAMPLE 32
6-Ethyl-2-anilinocarbonyl-1,4-benzodioxin

EXAMPLE 33
6-Hydroxy-2-(3,4,5-trimethoxyanilinocarbonyl)-1,4-benzodioxin

EXAMPLE 34
6-Hydroxy-7-tert-butyl-2-(N-methyl-N-benzylaminocarbonyl)-2,3-dihydro-1,4-benzodioxin

EXAMPLE 35
6-Hydroxy-2-(quinol-3-ylaminocarbonyl)-1,4-benzodioxin

EXAMPLE 36
6-Hydroxy-2-(pyridin-2-ylaminocarbonyl)-1,4-benzodioxin

EXAMPLE 37
6-Hydroxy-2-[(2,4-dimethylpyridin-6-yl)aminocarbonyl]-1,4-benzodioxin

EXAMPLE 38
6-Hydroxy-7-tert-butyl-2-[(2,4-dimethylpyridin-6-yl)aminocarbonyl]-1,4-benzodioxin

EXAMPLE 39
6-Hydroxy-2-(4-propylpiperazin-1-ylcarbonyl)-2,3-dihydro-1,4-benzodioxin

EXAMPLE 40
7-Hydroxy-2-[4-(4-fluorophenyl)piperazin-1-ylcarbonyl]-2,3-dihydro-1,4-benzodioxin

EXAMPLE 41
6-Hydroxy-2-[4-(pyrimid-2-yl)piperazin-1-ylcarbonyl]-1,4-benzodioxin

EXAMPLE 42
6-Hydroxy-2-(4-benzylpiperazin-1-ylcarbonyl)-1,4-benzodioxin

EXAMPLE 43
6-Hydroxy-2-[4-(4-fluorobenzoyl)piperazin-1-ylcarbonyl]-1,4-benzodioxin

EXAMPLE 44
6-Hydroxy-2-(4-phenethylpiperazin-1-ylcarbonyl)-1,4-benzodioxin

EXAMPLE 45
2-{4-[Bis-(4-fluorophenyl)methyl]piperazin-1-ylcarbonyl}-2,3-dihydro-1,4-benzodioxin

EXAMPLE 46
6-Hydroxy-2-{4-[bis-(phenyl)methyl]piperazin-1-ylcarbonyl}-1,4-benzodioxin

EXAMPLE 47
6-Acetyl-2-{4-[bis-(4-fluorophenyl)methyl]piperazin-1-ylcarbonyl}-1,4-benzodioxin

EXAMPLE 48
7-Acetyl-2-{4-[bis-(4-fluorophenyl)methyl]piperazin-1-ylcarbonyl}-1,4-benzodioxin

EXAMPLE 49 AND 50
The following are obtained by proceeding as for Preparation 5:

EXAMPLE 49
6-Acetyl-1,4-benzodioxin-2-carboxamide
The compound is prepared starting from ethyl 6-acetyl-1,4-benzodioxin-2-carboxylate.

EXAMPLE 50
6-Acetyl-2,3-dihydro-1,4-benzodioxin-2-carboxamide
The compound is prepared starting from ethyl 6-acetyl-2,3-dihydro-1,4-benzodioxin-2-carboxylate.

EXAMPLE 51
6-METHOXY-2-{4-[BIS-(4-FLUOROPHENYL)METHYL]PIPERAZIN-1-YLCARBONYL}-1,4-BENZODIOXIN

Add 0.98 mmol of 60% sodium hydride suspended in oil to a solution of 0.82 mmol of 6-hydroxy-2-{4-[bis-(4-fluorophenyl)methyl]piperazin-1-ylcarbonyl}-1,4-benzodioxin in 10 cm³ of N,N-dimethylformamide under a nitrogen atmosphere. Stir for 15 minutes at room temperature, then add dropwise 0.98 mmol of methyl iodide. Stir for 2 hours at room temperature and then concentrate to dryness under reduced pressure and purify the resulting crude product by chromatography on a silica column (eluant:petroleum ether/ethyl acetate, 50:50). 6-Methoxy-2-{4-[bis-(4-fluorophenyl)methyl]piperazin-1-ylcarbonyl}-1,4-benzodioxin is thereby obtained in a yield of 83%.

Melting point: 65° C.

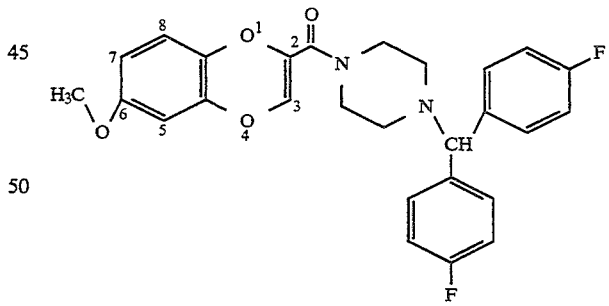

¹H NMR (CDCl₃), δ (ppm): 7.34 (dd, 4H, 2×H$_{2'}$, H$_{6'}$, J$_{2',3'}$=8.63 Hz, J$_{2',F}$=5.4 Hz); 6.98 (t, 4H, 2×H$_{3'}$, J$_{5'}$, J$_{3',2'}$=J$_{3',F}$=8.36 Hz); 6.56 (d, 1H, H$_8$, J$_{8,7}$=8.8 Hz); 6.56 (s, 1H, H$_3$); 6.36 (dd, 1H, H$_7$, J$_{7,8}$=8.8 Hz, J$_{7,5}$=2.9 Hz); 6.28 d, 1H, H$_5$, J$_{5,7}$=2.9 Hz); 4.25 (s, 1H, NCHAr); 3.70 (s, 3H, CH$_3$O); 3.72–3.66 (m, 4H$_{piperazine}$); 2.5–2.3 (m,4H$_{piperazine}$). IR(KBr)ν(cm-1): 1660 (C=O), 1605 (C=C), 1575–1485 (C=CAr), 1215-1190-1125-1080 (=C—O—C).

That compound can also be obtained by reacting 1-[bis-(4-fluorophenyl)methyl]piperazine with 6-methoxy-1,4-benzodioxin-2-carboxylic acid under the conditions of Example 1.

EXAMPLE 52

7-METHOXY-2-{4-[BIS-(4-FLUOROPHENYL)METHYL]PIPERAZIN -1- YLCARBONYL}-1,4-BENZODIOXIN

That compound is obtained in a yield of 78% starting from 7-hydroxy-2-{4-[bis-(4-fluorophenyl)methyl]piperazin-1-ylcarbonyl}-1,4-benzodioxin in accordance with the conditions in Example 51.

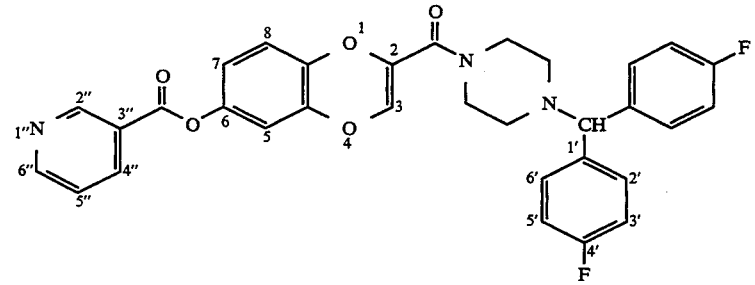

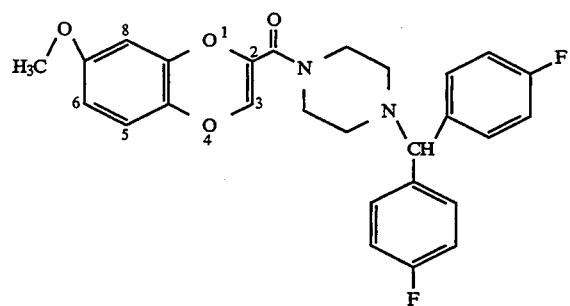

$^1$H NMR (CDCl$_3$), δ (ppm): 7.34 (dd, 4H, 2×H$_{2'}$, H$_{6'}$, J$_{2',3'}$=8.29 Hz, J$_{2',F}$5.53 Hz); 6.98 (t, 4H, 2×H$_{3'}$, H$_{5'}$, J$_{3',2'}$=J$_{3',F}$=8.29 Hz); 6.62 (d, 1H, H$_5$, J$_{5,6}$=9.1 Hz); 6.6 (s, 1H, H$_3$); 6.36 (dd, 1H, H$_6$, J$_{6,5}$=9.1 Hz, J$_{6,8}$=2.96 Hz); 6.23 (d, 1H, H$_8$, J$_{8,6}$=2.96 Hz); 4.27 (s, 1H, NCHAr); 3.71 (s, 3H, CH$_3$O); 3.7–3.66 (m, 4H$_{pipérazine}$); 2.45–2.4 (m, 4H$_{piperazine}$).

EXAMPLE 53

6-NICOTINOYLOXY-2-{4-[BIS-(4-FLUOROPHENYL) METHYL]PIPERAZIN-1-YLCARBONYL}-1,4-BENZODIOXIN

Heat at reflux for 8 hours, under a nitrogen atmosphere, a solution of 1.37 mmol of 6-hydroxy -2-{4-[bis-(4-fluorophenyl)methyl]piperazin-1-ylcarbonyl}-1,4-benzodioxin, 4.5 mmol of nicotinoyl chloride and 3.42 mmol of anhydrous pyridine in 25 cm$^3$ of dichloroethane. After cooling, the reaction mixture is washed with a saturated aqueous solution of sodium hydrogen carbonate, dried over magnesium sulfate and then concentrated under reduced pressure. The crude product is then purified by chromatography on a silica column (eluant:petroleum ether/ethyl acetate, 70:30). 6-Nicotinoyloxy-2-{4-[bis-(4-fluorophenyl)methyl]piperazin-1-ylcarbonyl}-1,4-benzodioxin is thereby obtained in a yield of 95%.

Melting point: 142° C.

$^1$H NMR (CDCl$_3$), δ (ppm): 9.32 (d, 1H$_{pyridine}$, H$_{2''}$, J$_{2'',6''}$=1.9 Hz); 8.94 (dd, 1H$_{pyridine}$, H$_{6''}$, J$_{6'',2''}$=1.9 Hz. J$_{6'',5''}$=5.1 Hz); 8.39 (ddd, 1H$_{pyridine}$, H$_{4''}$, J$_{4'',5''}$=8 Hz, J$_{4'',2''}$=2 Hz); 7.45 (dd, 1H$_{pyridine}$, H$_{5''}$, J$_{5'',6''}$=5.1 Hz, J$_{5'',4''}$=8 Hz); 7.35 (dd, 4H, 2×H$_{2'}$, H$_{6'}$, J$_{2',3'}$=8.5 Hz, J$_{2',F}$ =5.35 Hz); 6.99 (t, 4H, 2×H$_{3'}$, H$_{5'}$, J$_{3',2'}$=J$_{3',F}$=8.5 Hz); 6.75–6.62 (m, 3H, H$_8$, H$_7$, H$_5$); 6.58 (s, 1H, H$_3$); 4.26 (s, 1H, NCHAr); 3.7–3.5 (m, 4H$_{pipérazine}$); 2.6–2.3 (m, 4H$_{piperazine}$). IR(KBr)υ(cm-1): 2950–2740 (CH$_3$, CH$_2$), 1740 (C=O), 1675 (C=O), 1615 (C=C), 1265–1165 (=C—O—C).

EXAMPLE 54

7-NICOTINOYLOXY-2-{4-[BIS-(4-FLUOROPHENYL)METHYL]PIPERAZIN-1-YLCARBONYL}-1,4-BENZODIOXIN

That compound is obtained in a yield of 78% starting from 7-hydroxy-2-{4-[bis-(4-fluorophenyl)methyl]piperazin-1-ylcarbonyl}-1,4-benzodioxin and nicotinoyl chloride by proceeding as for Example 53.

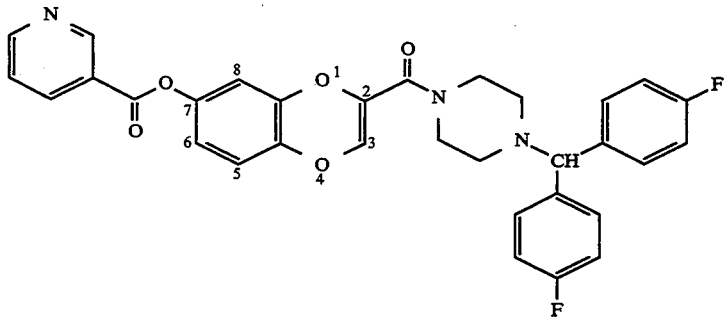

$^1$H NMR (CDCl$_3$), δ (ppm): 9.33 (d, 1H$_{pyridine}$, H$_{2'}$, J$_{2'',6''}$=2.19 Hz); 8.85 (dd, 1H$_{pyridine}$, H$_{6''}$, J$_{6'',5''}$=4.9 Hz, J$_{6'',4''}$=1.8 Hz); 8.38 (ddd, 1H$_{pyridine}$, H$_{4''}$, J$_{4'',6''}$=1.8 Hz, J$_{4'',5''}$=7.9 Hz); 7.45 (dd, 1H$_{pyridine}$, H$_{5'}$, J$_{5'',4''}$=7.9 Hz, J$_{5'',6''}$=4.9 Hz); 7.33 (dd, 4H, 2×H$_{2'}$, H$_{6'}$, J$_{2',3'}$=8.6 Hz, J$_{2',F}$=5.44 Hz); 6.98 (t, 4H, 2×H$_{3'}$, H$_{5'}$, J$_{3',2'}$=J$_{3',F}$=8.6 Hz); 6.75–6.73 (m, 2H, H$_3$, H$_5$); 6.63–6.61 (m, 2H, H$_8$, H$_6$); 4.25 (s, 1H, N—CH—Ar); 3.69–3.63 (m, 4H$_{piperazine}$); 2.42–2.37 (m, 4H$_{piperazine}$).

The following are also obtained by proceeding as for Example 53:

EXAMPLE 55

6-BENZOYLOXY-2-(N-BUTYLANILINOCARBONYL)-1,4-BENZODIOXIN

EXAMPLE 56

6-(3,4,5-TRIMETHOXYBENZOYLOXY)-2-(N-BUTYLANILINOCARBONYL )-1,4-BENZODIOXIN

EXAMPLE 57

6-PROPANOYLOXY-2-{4-[BIS-(4-FLUOROPHENYL)METHYL]PIPERAZIN-1-YLCARBONYL}-1,4-BENZODIOXIN

EXAMPLE 58

6-HYDROXY-2-{4-[BIS-(4-FLUOROPHENYL)METHYL]PIPERAZIN-1- YLMETHYL}-1,4-BENZODIOXIN

Under a nitrogen atmosphere, heat at reflux for 3 hours, in the presence of 5 mmol of lithium aluminium hydride, a solution of 2 mmol of 6-hydroxy-2-{4-[bis-(4-fluorophenyl)methyl]piperazin-1-ylcarbonyl}-1,4-benzodioxin in 35 cm³ of diethyl ether. After cooling, hydrolysis, removal of the insoluble mineral compounds by filtration and drying over magnesium sulfate, the compound obtained is purified by chromatography on a column of silica (eluant:petroleum ether/ethyl acetate, 40:60). 6-Hydroxy-2-{4-[bis-(4-fluorophenyl)methyl]-piperazin -1-ylmethyl}-1,4-benzodioxin is thereby obtained in a yield of 85%.

Melting point: 190° C.

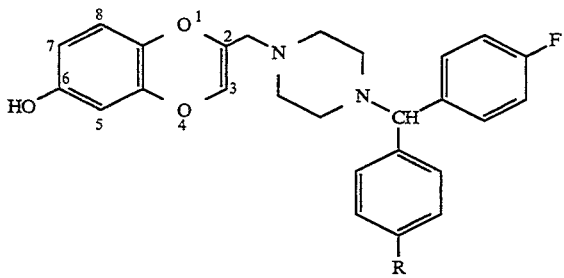

$^1$H NMR (CDCl$_3$) δ (ppm): 9 (s, 1H, OH) ;7.34 (dd, 4H, 2×H$_{2'}$, H$_{6'}$, J$_{2',3'}$=8.61 Hz, J$_{2',F}$=5.55 Hz); 6.96 (t, 4H, 2×H$_{3'}$, H$_{5'}$, J$_{3',2'}$=J$_{3',F}$=8.61 Hz); 6.48 (d, 1H, H$_8$, J$_{8,7}$=8.54 Hz); 6.23 (dd, 1H, H$_7$, J$_{7,8}$=8.54 Hz, J$_{7,5}$=2.87 Hz); 6.14 (d, 1H, J$_{5,7}$=2.87 Hz); 5.79 (s, 1H, H$_3$); 4.23 (s, 1H, NCHAr); 2.89 (s, 2H, CH$_2$N); 2.63–2.36 (m, 8H$_{piperazine}$). IR(KBr)υ(cm-1): 3610–2985 (OH), 1695 (C═C), 1595–1495 (C═CAr), 1210–1180–1135–1075 (═C—O—C).

The following compounds are obtained by proceeding in the same manner:

EXAMPLE 59

7-HYDROXY-6-TERT-BUTYL-2-{4-[BIS-(4-FLUOROPHENYL)METHYL]PIPERAZIN-1-YLMETHYL}-2,3-DIHYDRO-1,4-BENZODIOXIN

That compound is obtained in a yield of 65% starting from 7-hydroxy-6-tert-butyl-2-{4-[bis-2-(4-fluorophenyl)methyl]piperazin-1-ylmethyl}-2,3-dihydro-1,4-benzodioxin.

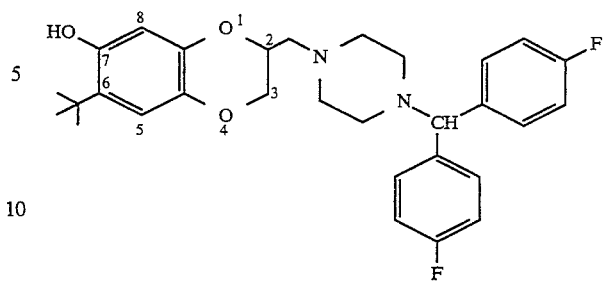

$^1$H NMR (CDCl$_3$), δ (ppm)+D$_2$O: 7.32 (dd, 4H, 2×H$_{2'}$, H$_{6'}$, J$_{2',3'}$=8.45 Hz, J$_{2',F}$=5.88 Hz); 6.96 (t, 4H, 2×H$_{3'}$, H$_{5'}$, J$_{3',2'}$=J$_{3',F}$=8.45 Hz); 6.75 (s, 1H, H$_5$); 6.26 (s, 1H, H$_8$); 4.41–4.29 (m, 1H, H$_2$); 4.18 (s, 1H, N—CH—Ar); 4.16 (dd, 1H, H$_{3b}$, J$_1$=11.4 J$_3$=1.47 Hz); 3.86 (dd, 1H, H$_{3b}$, J$_1$=11.4 Hz, J$_2$=6.62 Hz); 2.65–2.42 (m, 10H, 8H$_{piperazine}$+CH$_2$—N); 1.35 (s, 9H, (CH$_3$)$_3$C).

EXAMPLE 60

7-HYDROXY-6-TERT-BUTYL-2-{4-[BIS-(4-FLUOROPHENYL)METHYL]PIPERAZIN-1-YLMETHYL}-1,4-BENZODIOXIN

That compound is obtained in a yield of 86% starting from 7-hydroxy-6-tert-butyl-2-{4-[bis(4-fluorophenyl)methyl]piperazin-1-ylmethyl}-1,4-benzodioxin.

Melting point: 186° C.

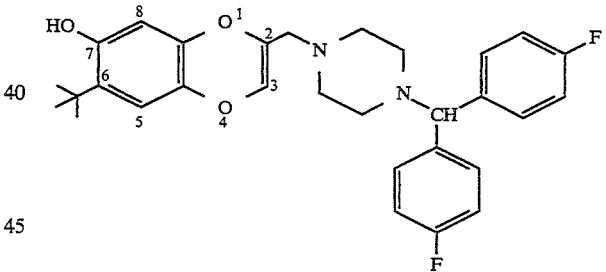

$^1$H NMR (CDCl$_3$), δ (ppm): 7.33 (dd, 4H, 2×H$_{2'}$, H$_{6'}$, J$_{2',3'}$=8.46 Hz, J$_{2',F}$=5.15 Hz); 6.98 (t, 4H, 2×H$_{3'}$, H$_{5'}$, J$_{3',2'}$=J$_{3',F}$=8.46 Hz); 6.56 (s, 1H, H$_3$); 6.45 (s, 1H, H$_5$); 6.23 (s, 1H, OH); 6.20 (s, 1H, H$_8$); 4.23 (s, 1H, NCHAr); 3.67–3.60 (m, 4H$_{piperazine}$); 2.40–2.33 (m, 6H, 4H$_{piperazine}$+CH$_2$—N); 1.31 (s, 9H, (CH$_3$)$_3$C). IR(KBr)υ(cm-1): 3610–3280–3100–3000 (OH), 1595–1495 (C═C).

EXAMPLE 61

6-HYDROXY-7-TERT-BUTYL-2-{4-[BIS-(4-FLUOROPHENYL)METHYL]PIPERAZIN-1-YLMETHYL}-2,3-DIHYDRO-1,4-BENZODIOXIN

That compound is obtained in a yield of 73% starting from 6-hydroxy-7-tert-butyl-2-{4-[bis(4-fluorophenyl)methyl]piperazin-1 -ylmethyl}-2,3-dihydro-1,4-benzodioxin.

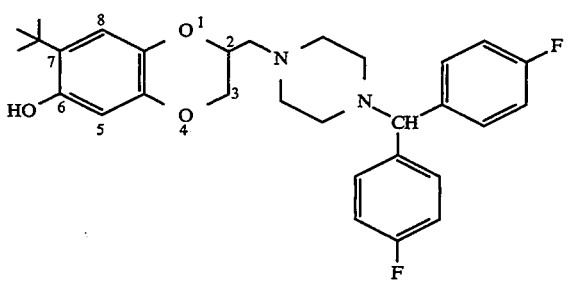

$^1$H NMR (CDCl$_3$), δ (ppm): 7.33 (dd, 4H, 2×H$_{2'}$, H$_{6'}$, J$_{2',3'}$=8.8 Hz, J$_{2',F}$=5.15 Hz); 6.96 (t, 4H, 2×H$_{3'}$, H$_{5'}$, J$_{3',2'}$=J$_{3',F}$=8.8 Hz); 6.76 (s, 1H, H$_8$); 6.24 (s, 1H, H$_5$); 4.28–4.15 (m, 3H, H$_2$, H$_{3a}$, NCHAr); 2.7–2.51 (m, 6H, 4H$_{piperazine}$, CH$_2$N); 2.5–2.2 (m, 4H$_{piperazine}$); 1.37 (s, 9H, (CH$_3$)$_3$C).

The following are also obtained in the same manner:

EXAMPLE 62
6-HYDROXY-2-(N-BUTYLANILINOMETHYL)-1,4-BENZODIOXIN

EXAMPLE 63
6-HYDROXY-7-TERT-BUTYL-2-(N-BUTYLANILINOMETHYL)-1,4-BENZODIOXIN

EXAMPLE 64
6-HYDROXY-7-TERT-BUTYL-2-(N-BUTYLAMINOMETHYL)-2,3-DIHYDRO-1,4-BENZODIOXIN

EXAMPLE 65
6-METHOXY-2-{4-UBIS-(4-FLUOROPHENYL)-METHYL]PIPERAZIN-1-YLMETHYL}-1,4-BENZODIOXIN

EXAMPLE 66
6-HYDROXY-2-[(2,4-DIMETHYLPYRIDIN-6-YL)AMINOMETHYL]-1,4-BENZODIOXIN

EXAMPLE 67
6-ETHYL-2-ANILINOMETHYL-1,4-BENZODIOXIN

EXAMPLE 68
6-HYDROXY-2-[4-(PYRIMID-2-YL)PIPERAZIN-1-YLMETHYL]-1,4-BENZODIOXIN

EXAMPLE 69
7-HYDROXY-2-[4-(2,3,4-TRIMETHOXYBENZYL)-PIPERAZIN-1-YLMETHYL]-1,4-BENZODIOXIN

EXAMPLE 70
6-HYDROXY-7-TERT-BUTYL-2-PIPERIDINOMETHYL-1,4-BENZODIOXIN

EXAMPLE 71
6-HYDROXY-2-(4-PHENYLPIPERIDINOMETHYL)-1,4-BENZODIOXIN

EXAMPLE 72
6-HYDROXY-2-{4-[BIS-(4-FLUOROPHENYL)METHYLENE]PIPERIDINOMETHYL}-1,4-BENZODIOXIN

EXAMPLE 73
6-HYDROXY-2-(N,N-DIPROPYLAMINOMETHYL)-1,4-BENZODIOXIN

EXAMPLE 74
7-METHOXY-2-(N,N-DIPROPYLAMINOMETHYL)-2,3-DIHYDRO-1,4-BENZODIOXIN

EXAMPLE 75
7-HYDROXY-2-[4-(4-FLUOROPHENYL)PIPERAZIN-1-YLMETHYL]-2,3-DIHYDRO-1,4-BENZODIOXIN

EXAMPLE 76
2-{4-[BIS-(4-FLUOROPHENYL)METHYL]PIPERAZIN-1-YLTHIOCARBONYL}-1,4-BENZODIOXIN

Add 0.054 g (0.12 tool) of pentaphosphorus disulfide (P$_4$S$_{10}$) and 0.555 g (6.7 mmol) of solid sodium hydrogen carbonate in succession to 0.5 g (1.1 mmol) of the compound obtained in Example 9 dissolved in 8 ml of toluene and 2 ml of acetonitrile, under an inert atmosphere. Heat at reflux for 8 hours, then cool and wash abundantly with methylene chloride. After concentration of the reaction mixture to dryness under reduced pressure, the crude product is purified by chromatography on a silica column (eluant:petroleum ether/ethyl acetate, 70:30). The expected compound is obtained in a yield of 80%.

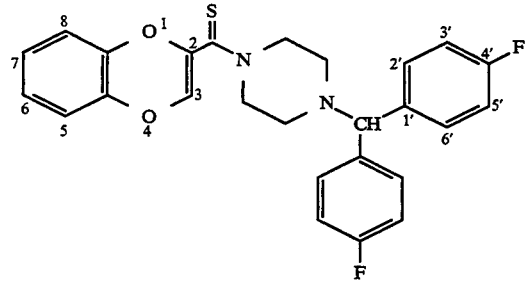

$^1$H NMR (CDCl$_3$), δ (ppm): 7.38 (dd, 4H, 2×H$_{2'}$, H$_{6'}$, J$_{2',3'}$=8.46 Hz, J$_{2',F}$=5.15 Hz); 7.01 (t, 4H, 2×H$_{3'}$, H$_{5'}$, J$_{3',2'}$=J$_{3',F}$=8.46 Hz); 6.89–6.58 (m, 5H, 4H$_{aromatic}$, H$_3$); 4.3 (s, 1H, NCHAr); 4.2–3.87 (m, 4H, H$_{piperazine}$); 2.67–2.43 (m, 4H$_{piperazine}$). IR(KBr)υ(cm-1): 1290 (C=S).

EXAMPLE 77
6-HYDROXY-2-14-[BIS(4-FLUOROPHENYL)METHYL]PIPERAZIN-1-YLTHIOCARBONYL}-1,4-BENZODIOXIN

METHOD A 17 mmols of the compound obtained in Example 1 are dissolved in 125 cm$^3$ of anhydrous toluene. 10.2 mmols of Lawessons's reagent are added and the whole is heated at reflux for 6 hours. After evaporation of the solvent and purification on a column of silica (eluant:dichloromethane), the product is obtained in a yield of 12% in the form of an oil.

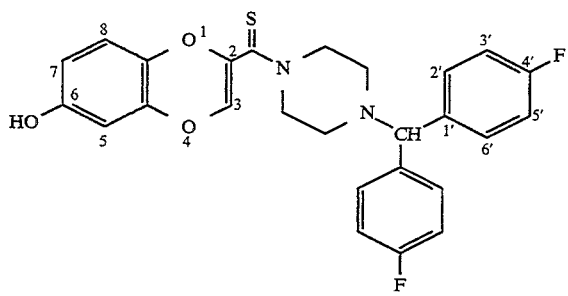

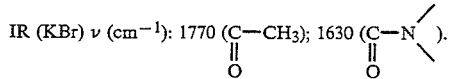

¹H NMR (CDCl₃), δ (ppm): 7.36 (dd, 4H, 2×H₂', H₆', $J_{2',3'}$=8.59 Hz, $J_{2',F}$=5.42 Hz); 7 (t, 4H, 2×H₃', H₅', $J_{3',2'}$=$J_{3',F}$=8.59 Hz); 6.6 (s, 1H, H₃); 6.48 (d, 1H, H₈, $J_{8,7}$=8.60 Hz); 6.30 (dd, 1H, H₇, $J_{7,5}$=2.89 Hz, $J_{7,8}$=8.60 Hz); 6.23 (d, 1H, H₅, $J_{5,7}$=2.89 Hz); 4.28 (s, 1H, NCHAr); 4.12–3.92 (m, 4H$_{piperazine}$); 3.45 (s, 1H, OH); 2.57–2.47 (m, 4H$_{piperazine}$). IR(KBr)υ(cm-1): 3600–2980–2600 (OH); 1280 (C=S).

METHOD B

Step 1:
6-Acetoxy-2-{4-[bis(4-fluorophenyl)methyl]piperazin-1-ylcarbonyl}-1,4-benzodioxin Dissolve 0.5 g (1.07 mmol) of the compound obtained in Example 1 at 0° C. in 0.255 ml (2.7 mmol) of acetic anhydride under an inert atmosphere. Add 2 volumes of pyridine (0.5 10 ml) and continue stirring while returning to room temperature for a period of 1 h 30. Neutralise with a saturated sodium hydrogen carbonate solution. After extraction with ether (2×25 ml), the product is purified by chromatography on a silica column (eluant:ethyl acetate/petroleum ether, 20:80) and obtained in pure form as a solid in a yield of 92%.

Melting point: 69° C.

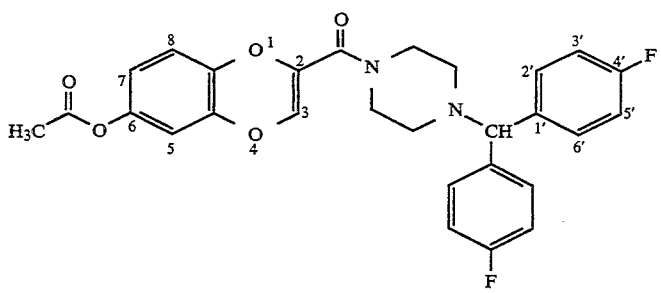

¹H NMR (CDCl₃), δ (ppm): 7.35 (dd, 4H, 2×H₂', H₆', $J_{2',3'}$=8.57 Hz, $J_{2',F}$=5.47 Hz); 6.93 (t, 4H, 2×H₅', H₃', $J_{3',2'}$=$J_{3',F}$=8.57 Hz); 6.63–6.61 (m, 2H, H₃, H₈, $J_{8,7}$=8.39 Hz); 6.57 (dd, 1H, H₇, $J_{7,5}$=2.48 Hz, $J_{7,8}$=8.39 Hz); 6.48 (d, 1H,H₅,₇=2.48 Hz); 4.25 (s, 1H, NCHAr); 3.7–3.60 (m, 4H$_{piperazine}$); 2.45–2.36 (m, 4H$_{piperazine}$); 2.25 (s, 3H, CH₃COO).

IR (KBr) υ (cm⁻¹): 1770 (C—CH₃, C=O); 1630 (C—N, C=O).

Step 2
6-Acetoxy-2-{4-[bis(4-fluorophenyl)methyl]piperazin-1-ylthiocarbonyl}-1,4-benzodioxin Dissolve 0.5 g (0.99 mmol) of the compound obtained in the preceding step in 8 ml of anhydrous toluene. Add 0.49 g (0.99 mmol) of Lawesson's reagent and heat at reflux for 12 hours. After concentration of the reaction mixture to dryness under reduced pressure, the product is purified by chromatography on a silica column (eluant:petroleum ether/ethyl acetate, 70:30). The thioamide is obtained in a yield of 78% as a foam.

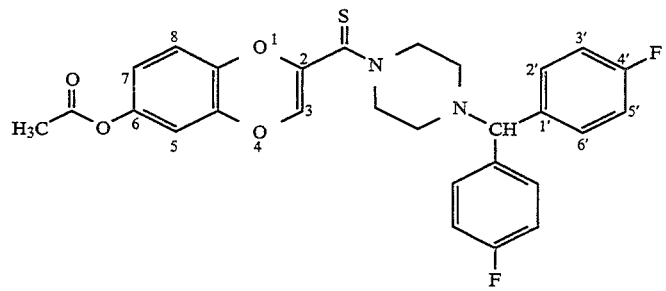

¹H NMR (CDCl₃), δ (ppm): 7.36 (dd, 1H, 2×H₂', H₆', $J_{2',F}$=5.41 Hz, $J_{2',3'}$=8.53 Hz); 7 (t, 2H, 2×H₃', H₅', $J_{3',2'}$=$J_{3',F}$=8.53 Hz); 6.65–6.6 (m, 2H, H₃, H₈, $J_{8,7}$=8.62 Hz); 6.75 (dd, 1H, H₇, $J_{7,5}$=2.47 Hz, $J_{7,8}$=8.62 Hz); 6.49 (d, 1H, H₅, $J_{5,7}$=2.47 Hz); 4.28 (s, 1H, NCHAr); 4.13–3.90 (m, 4H$_{piperazine}$); 2.56–2.45 (m, 4H$_{piperazine}$); 2.24 (s, 3H, CH₃COO). IR(film)υ(cm-1): 1765 (C=O); 1295 (C=S).

Step 3
6-Hydroxy-2-{4-[bis(4-fluorophenyl)methyl]-piperazin-1-ylthiocarbonyl}-1,4-benzodioxin Add 0.150 cm³ of a molar solution of sodium methanolate in methanol to a solution of 0.5 g of the acetoxylated thioamide compound above (0.96 mmol) in 5 cm³ of anhydrous methanol under a nitrogen atmosphere. Stir at room temperature for 3 hours and then neutralise with Dowex X-8 acid resin which has been washed beforehand with methanol. After filtration and evaporation in vacuo, the crude product obtained is purified by chromatography on a silica column (eluant-petroleum ether/ethyl acetate 30:70). The phenolic thioamide is thereby obtained in a yield of 90% in the form of an oil. Total yield from the 3 Steps: 64.5%.

The following are obtained in the same manner:

EXAMPLE 78

7-HYDROXY-6-TERT-BUTYL-2-{4-[BIS(4-FLUOROPHENYL)METHYL]PIPERAZIN-1-YLTHIOCARBONYL}-2,3-DIHYDRO-1,4-BENZODIOXIN

Obtained starting from the compound of Example 5.

EXAMPLE 79

6-HYDROXY-2-(N-BUTYLANILINOTIHOCARBONYL)-1,4-BENZODIOXIN

Obtained starting from the compound of Example 14.

EXAMPLE 80

7-HYDROXY-2-[4-(2,3,4-TRIMETHOXYBENZYL)-PIPERAZIN-1-YLTHIOCARBONYL]-1,4-BENZODIOXIN

Obtained starting from the compound of Example 16.

EXAMPLE 81

6-HYDROXY-2-(4-PHENYLPIPERIDINOTHIOCARBONYL)-1,4-BENZODIOXIN

Obtained starting from the compound of Example 21.

EXAMPLE 82

6-HYDROXY-2-[4-(4-FLUOROBENZOYL)-PIPERIDINOTHIOCARBONYL]-1,4-BENZODIOXIN

Obtained starting from the compound of Example 24.

EXAMPLE 83

6-HYDROXY-2-((QUINOLIN-3-YL)AMINOTHIOCARBONYL)-1,4-BENZODIOXIN

Obtained starting from the compound of Example 35.

EXAMPLE 84

6-(3,4,5-TRIMETHOXYBENZOYLOXY)-2-(N-BUTYLANILINOTHIOCARBONYL )-1,4-BENZODIOXIN

Obtained starting from the compound of Example 56.

EXAMPLE 85

6-NICOTINOYLOXY-2-{4-[BIS-(4-FLUOROPHENYL)METHYL]PIPERAZIN-1-YLTHIOCARBONYL}-1,4-BENZODIOXIN

Obtained starting from the compound of Example 53.

PHARMACOLOGICAL STUDY

EXAMPLE A

Study of the protective activity against LDL oxidation (electrophoretic method)

The capacity of the compounds of the invention to decrease the proportions of oxidised LDLs was measured by incubating a preparation comprising native human LDLs, a $Cu^{2+}$ free radical generator, and the compounds to be tested for 24 hours. The oxidation products are determined by FPLC (Fast Protein Liquid Chromatography) in accordance with the method described by B. Vedie et al., *Journal of Lipid Research*, 32, 1359–1369, (1991). By that method it was possible to identify 5 peaks corresponding to different degrees of LDL oxidation. Peaks A and B correspond to the native forms of LDL and peaks C, D and E correspond to the different states of oxidation of the LDLs (peak E corresponding to the most oxidised form). The results are expressed as a percentage of the LDLs corresponding to those different states of oxidation. A protective effect of a compound with respect to oxidation induced by copper is demonstrated by a displacement of the E form towards the D form, or even towards the C form or the B form for the most powerful compounds.

TABLE I

| Protective activity against LDL oxidation | | | | | |
|---|---|---|---|---|---|
| OXIDISED FORMS SEPARATED BY FPLC | A | B | C | D | E |
| Control without $Cu^{++}$ | 100% | | | | |
| Control with $Cu^{++}$ | | | | 75% | 25% |
| $Cu^{++}$ + probucol (10 μM) | | | | 80% | 20% |
| $Cu^{++}$ + compound of Example 1 (10 μM) | | 95% | 5% | | |

The compounds of the invention are remarkably active in that test with activities far superior to those ascertained for probucol which is used as a reference.

EXAMPLE B

Study of the protective activity against LDL oxidation (determination of malonic dialdehyde)

Purified human LDLs are incubated in the presence of copper sulfate at a concentration of $5.10^{-6}M$ in the absence or presence of the compounds being studied. The activity of the tested products is evaluated by calculating the concentration that reduces the production of malonic dialdehyde (MDA) by 50% ($IC_{50}$) compared with control experiments carried out in the absence of the product. The compounds of the invention are remarkably active in that test, with $IC_{50}$s (about $10^{-7}M$) very considerably lower than those determined for probucol.

EXAMPLE C

Measurement of haemolysis induced by AAPH

Human red blood corpuscles are placed for a period of 30 minutes at 37° C. in the presence of AAPH, which generates free radicals at a constant rate, and in the presence or absence of the compounds being studied. The optical density of the supernatant is measured at 403 nm compared with the control without AAPH. The percentage inhibition of haemolysis is calculated by comparison with the 100% haemolysis obtained for the AAPH control.

TABLE II

| | % inhibition at $10^{-5}$ M of AAPH haemolysis | | | | | | | |
|---|---|---|---|---|---|---|---|---|
| EXAMPLE | 1 | 2 | 3 | 10 | 11 | 12 | 13 | 17 |
| Inhibition | 62% | 100% | 88% | 100% | 100% | 100% | 100% | 100% |

The compounds according to the invention thus demonstrate a remarkable cell-protecting activity against the toxicity of the radicals induced by AAPH.

EXAMPLE D

Demonstration of antihypoxic activity in vivo

Male mice (Swiss CD 1 ) weighing from 25 to 30 g are, before any experiment, housed for one week under conditions customary for animals (20°–22° C., 55% humidity, light/darkness cycle 12/12, commercial feed and water as desired). The mice are placed in a box (7×5×5 cm) in which an atmosphere poor in oxygen is created by passing through a stream of air (96% $N_2$, 4% $O_2$, 12 l/min). The time taken until the first signs of suffocation (or "gasps") occur is measured. The mice receive a dose of the compounds to be tested by the intraperitoneal route 30 minutes before the hypoxia is induced. Vincamine is used as the reference drug.

TABLE III

Demonstration of the antihypoxic activity

| TREATMENT | DOSE (mg/kg) | TIME UNTIL THE FIRST GASPS OCCUR (in seconds) |
|---|---|---|
| Control | — | 36 ± 4 |
| Vincamine | 2,5 | inactive |
| Vincamine | 20 | 147 ± 14 (significant) |
| Example 1 | 2,5 | 108 (significant) |
| Example 10 | 2,5 | 97 (significant) |

The results show that the compounds of the invention are significantly active in that test at doses far below those of vincamine (reference product).

EXAMPLE E

Measurement of lipoxygenase activities The measurements are carried out on rabbit granulocytes. The isolated granulocytes are stimulated in vitro by the calcium ionophore A 23 187. The B4 leukotrienes released in the extracellular medium are measured by Radio Immuno Assay (RIA). The results (average of 3 independent measurements) are expressed as a percentage inhibition compared with the control.

In that study the compound of Example 1 (10 µM) exhibits an inhibiting activity of 62%.

EXAMPLE F

Measurement of antiaggregation activity

In that study, the compounds of the invention (100 µ/ml) were tested with the aim of quantifying their ability to inhibit the maximum non-reversible platelet aggregation (rabbit plasma rich in platelets) induced by sodium arachidonate (50 µ/ml). Thus the minimum active concentration for the compound of Example 1 is 20 µM.

EXAMPLE G

Anticalcic activity

The anticalcic activity was studied in the thoracic aorta of male Wistar rats. Once they have been introduced into experimental vessels containing a physiological solution, the vascular rings are subjected to an initial tension of 2 g. The preparations are then placed in the presence of a hyperpotassic solution (60 mM of potassium chloride) in order to obtain a sustained contractile response. Increasing concentrations of the product being tested are then added for the period necessary to obtain a stable effect.

Each compound of the invention is thus tested in 2 preparations at 8 concentrations ($10^{-8}$M to $3\times10^{-5}$M) to obtain a concentration-effect curve and determine the $IC_{50}$.

TABLE IV

Inhibition of the concentration of the thoracic aorta of rats induced by potassium chloride

| Example | $IC_{50}$ (µM) |
|---|---|
| 1 | 0,5 |
| 58 | 0,6 |

EXAMPLE H

Hypolipaemic activity

Groups each comprising 6 mice are rendered hypercholesterolaemic by a diet that is high in cholesterol and in cholic acid for 7 days. The compounds of the invention are administered p.o. (100 mg/kg) on the 6th and 7th day (half the dose being administered on day 6 and the other half on day 7). The animals are then left without food and drink for one night. The reduction in the concentration of cholesterol in the serum compared with hypercholesterolaemic control mice is then evaluated, as is also the reduction in concentration of lipoproteins (corresponding to the LDL-VLDL fractions), after precipitation by the addition of heparin to the serum, in the same hypercholesterolaemic mice compared with the control animals.

The compound of Example 58 caused a significant reduction in the total cholesterol (33% at 100 mg/kg p.o.) and a significant reduction in the LDL-VLDL fraction (35% at 100 mg/kg p.o.).

EXAMPLE I

Serotoninergic activity

The experiments are carried out on membranes prepared from the cerebral cortex of male Wistar rats (CERJ, le Genest St Isle). The binding measurements are carded out using ketanserine as reference compound. The conditions of the experiment are summarised below:

| Receptor | Ligand | Concentrations | Non-specifics | Incubation |
|---|---|---|---|---|
| 5-$HT_2$ | [$^3$H]ketanserine | 0.5 nM | ketanserine (1 µM) | 40 min/25° C. |

After incubation, the membranes are quickly filtered. The filtrates are then transferred to flasks containing scintillation liquid and the bound radioactivity is determined by a liquid scintillation counter (LS6000, Beckman). The affinity of the compounds of the invention for the 5-$HT_2$ receptors is evaluated, at the concentration 10 µM (n=3), using competition experiments. Under those conditions the compound of Example 58 demonstrated an inhibiting activity of 79%.

EXAMPLE J

Pharmaceutical composition: tablets

| Preparation formula for 1000 50 mg tablets | |
|---|---|
| Compound of Example 1 | 50 g |
| wheat starch | 15 g |
| maize starch | 15 g |
| lactose | 65 g |
| magnesium stearate | 2 g |
| silica | 1 g |
| hydroxypropyl cellulose | 2 g |

We claim:

1. A compound selected from those of formula (I):

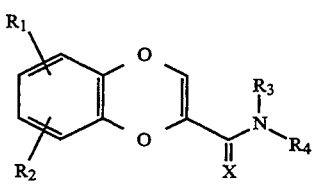

wherein:

R₁ and R₂, which are the same or different, are each selected, independently of the other, from hydrogen, alkyl having 1 to 6 carbon atoms inclusive in straight or branched chain, hydroxy, alkoxy having 1 to 5 carbon atoms inclusive in straight or branched chain, a group:

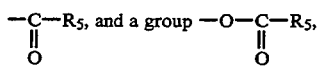

wherein R₅ is selected from alkyl having 1 to 5 carbon atoms inclusive in straight or branched chain, optionally substituted aryl selected from phenyl and naphthyl, optionally substituted aralkyl selected from phenyl and naphthyl attached to an alkyl chain having 1 to 4 carbon atoms inclusive, optionally substituted pyridyl, inclusive, R₃ and R₄, which are the same or different, are each selected, independently of the other, from hydrogen, alkyl having 1 to 5 carbon atoms inclusive in straight or branched chain and being optionally substituted, and phenyl and benzyl each of which may optionally be substituted by one or more chemical entities selected from the radicals defined for R₁ or R₂, or R₃ and R₄, together with the nitrogen atom to which they are attached, form a heterocycle of formula (I')

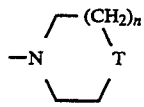

wherein n is selected from 0, 1, 2 and 3,

T is selected from oxygen, the group

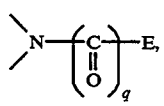

- the group 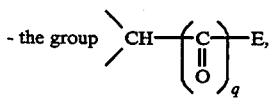

- and the group 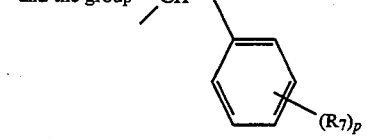

wherein:

m and p, which are the same or different, each independently represents the value 0, 1, 2, 3, 4, or 5, R₆ and R₇, which are the same or different, are each selected, independently of the other, from halogen, hydroxy, straight-chain or branched alkyl having 1 to 5 carbon atoms inclusive, alkoxy, haloalkyl, and polyhaloalkyl, q is selected from 0 and 1, E is selected from hydrogen, alkyl having 1 to 5 carbon atoms inclusive in straight or branched chain, aryl, and aralkyl, and the group:

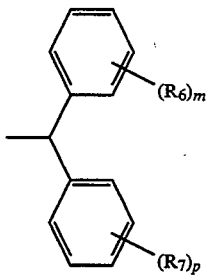

wherein R₆, R₇, m and p are as defined hereinbefore, with the proviso that, when X=O and R₁=R₂=H, T cannot represent CH₂ or quinazolinyl-2-ylamino, and X is selected from O, S and H₂, it being understood that, unless indicated otherwise, the expression "optionally substituted" indicates an optional substitution by one or more radicals selected from hydroxy, nitro, cyano, alkyl, alkoxy, acyl, haloalkyl, polyhaloalkyl, amino, alkylamino and dialkylamino, the alkyl chains of the alkyl, alkoxy, acyl, haloalkyl, polyhaloalkyl, alkylamino and dialkylamino groups having 1 to 5 carbon atoms inclusive in straight or branched chain, their possible stereoisomers, N-oxides, and pharmaceutically-acceptable addition salts with an acid or a base.

2. A compound according to claim 1 selected from those, wherein X represents oxygen, their possible stereoisomers, N-oxides, and pharmaceutically-acceptable addition salts with an acid or a base.

3. A compound according to claim 1 selected from those, wherein X represents sulfur, their possible stereoisomers, N-oxides, and pharmaceutically-acceptable addition salts with an acid or a base.

4. A compound according to claim 1 selected from those, wherein X represents H₂, their possible stereoisomers, N-oxides, and pharmaceutically-acceptable addition salts with an acid or a base.

5. A compound according to claim 1 selected from those, wherein R₃ and R₄, together with the nitrogen atom to which they are attached, form a substituted piperazinyl radical, their possible stereoisomers, N-oxides, and pharmaceutically-acceptable addition salts with an acid or a base.

6. A compound according to claim 1 selected from 6-hydroxy-2-{4-[bis-(4-fluorophenyl)methyl]piperazin-1-ylcarbonyl}-1,4-benzodioxin, and pharmaceutically-acceptable addition salts thereof with an acid or a base.

7. A compound according to claim 1 selected from 6-hydroxy-7-tert-butyl-2-{4-[bis-(4-fluorophenyl)methyl]piperazin-1-ylcarbonyl}-1,4-benzodioxin, and pharmaceutically-acceptable addition salts thereof with an acid or a base.

8. A compound according to claim 1 selected from 6-hydroxy-2-{4-[bis-(4-fluorophenyl)methyl]piperazin-1-ylmethyl}-1,4-benzodioxin, and pharmaceutically-acceptable addition salts thereof with an acid or a base.

9. A compound according to claim 1 selected from 6-hydroxy-2-(N-butylanilinocarbonyl)-1,4-benzodioxin, and pharmaceutically-acceptable addition salts thereof with an acid or a base.

10. A compound selected from those of formula (XI) which are useful as intermediates in the preparation of compounds of formula (I):

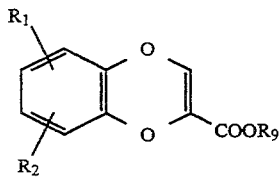

wherein:

$R_1$ and $R_2$, which are the same or different, are each selected, independently of the other, from hydrogen, alkyl having 1 to 5 carbon atoms inclusive in straight or branched chain, hydroxy, alkoxy having 1 to 5 carbon atoms inclusive in straight or branched chain, a group:

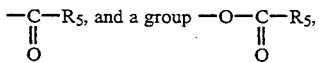

wherein $R_5$ is selected from alkyl having 1 to 5 carbon atoms inclusive in straight or branched chain, optionally substituted aryl selected from phenyl and naphthyl, optionally substituted aralkyl selected from phenyl and naphthyl attached to an alkyl chain having 1 to 4 carbon atoms inclusive, optionally substituted, pyridyl, inclusive, $R_9$ is selected from hydrogen and alkyl having 1 to 5 carbon atoms inclusive in straight or branched chain, with the following proviso when $R_1$ and $R_2$ each represents hydrogen $R_9$ cannot represent ethyl, and also their possible stereoisomers.

11. A method for treating a mammal afflicted with a disease requiring an anti-oxidant having a protective activity in lipid peroxidation processes, comprising the step of administering to said mammal an amount of a compound of claim 1 which is effective for alleviation of said disease.

12. A pharmaceutical composition useful in treating a disease requiring an antioxidant, which contains as active ingredient an effective antioxidant amount of a compound according to claim 1, in combination with a pharmaceutically-acceptable excipient or vehicle.

* * * * *

UNITED STATES PATENT AND TRADEMARK OFFICE
CERTIFICATE OF CORRECTION

PATENT NO. : 5,420,132

DATED : May 30, 1995

Page 1 of 4

INVENTOR(S) : Gèrald Guillaumet, Gèrard Coudert, Valèrie Thiery, Gèrard Adam, Jean-Guy-Bizot-Espiard, Bruno Pfeiffer, Pierre Renard It is certified that error appears in the above-indentified patent and that said Letters Patent is hereby corrected as shown below:

Column 2, line 5; delete the "15"
Column 4, line 57; "OID" should read -- (III) --
Column 4, line 60; "(lift" should read -- (IIf --
Column 5, approximately line 7; formula identification "(Va)" should read formula identifcation -- X --
Column 12, line 31; "6,6" should read -- 6.6 --
Column 13, line 54; "(rid," should read -- (dd, --
Column 13, line 55; "$J_{7.8}$" should read -- $J_{7.8}$ --
Column 16, line 38; "$J_{3.2}$" should read -- $J_{3.2}$ --
Column 16, line 49; insert a -- * -- before the word "ethyl" at the beginning of the line.
Column 16, line 64; "$H_3b$)." should read -- $H_{3b}$). --
Column 16, line 65; insert a -- * -- before the word "ethyl" at the beginning of the line.
Column 17, line 13; insert a -- * -- before the word "ethyl" at the beginning of the line.
Column 17, line 30; insert a -- * -- before the word "ethyl" at the beginning of the line.
Column 17, line 47; insert a -- * -- before the word "ethyl" at the beginning of the line.
Column 17, line 62; "$^1$NMR" should read -- $^1$H NMR --
Column 17, line 64; "4.24.0" should read -- 4.2-4.0 --
Column 17, line 65; insert a -- * -- before the word "ethyl" at the beginning of the line.
Column 18, line 12; insert a -- * -- before the word "ethyl" at the beginning of the line.
Column 18, line 29; insert a -- * -- before the word "ethyl" at the beginning of the line.
Column 19, line 18; "(DIMSO)," should read -- (DMSO), --
Column 19, line 60; "$H_{3+}$," should read -- $H_{3'}$, --
Column 20, line 61; "6.23" should read -- 6.32 --
Column 20, line 65; "3.2" should read -- 3.5 --

UNITED STATES PATENT AND TRADEMARK OFFICE
CERTIFICATE OF CORRECTION

PATENT NO. : 5,420,132
DATED : May 30, 1995
INVENTOR(S) : Gèrald Guillaumet, Gèrard Coudert, Valèrie Thiery, Gèrard Adam, Jean-Guy-Bizot-Espiard, Bruno Pfeiffer, Pierre Renard It is certified that error appears in the above-indentified patent and that said Letters Patent is hereby corrected as shown below:

Column 21, approximately line 28; 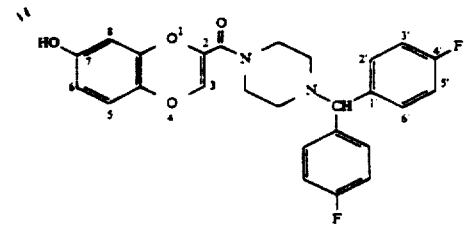

should read 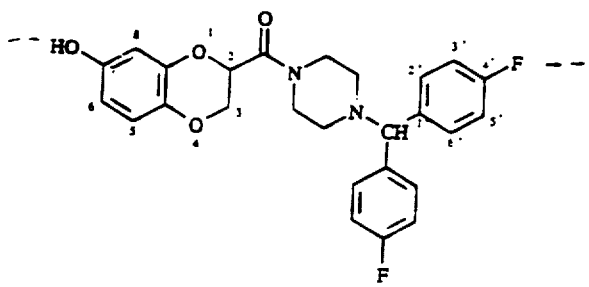

Column 22, line 24; "127" should read -- 1.27 --
Column 22, line 31; "-I," should read -- -1, --
Column 23, approximately line 40; 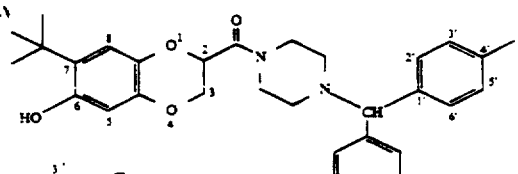

should read 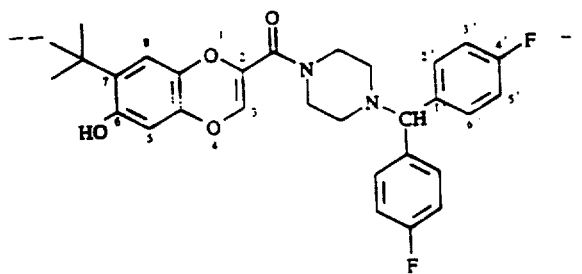

UNITED STATES PATENT AND TRADEMARK OFFICE
CERTIFICATE OF CORRECTION

PATENT NO. : 5,420,132

DATED : May 30, 1995

Page 3 of 4

INVENTOR(S) : Gèrald Guillaumet, Gèrard Coudert, Valèrie Thiery, Gèrard Adam, Jean-Guy-Bizot-Espiard, Bruno Pfeiffer, Pierre Renard It is certified that error appears in the above-indentified patent and that said Letters Patent is hereby corrected as shown below:

Column 23, line 54; "8.32" should read -- 8.35 --
Column 23, line 63; "METHYLIPIPER-" should read -- METHYL]PIPER- --
Column 24, line 56; "1.4-" should read -- 1,4- --
Column 25, line 14; "frown" should read -- from --
Column 25, line 40; "BENZOP" should read -- BENZO --
Column 25, line 55; "$^1$H(CDCl$_3$," should read -- $^1$H NMR(CDCl$_3$, --
Column 25, line 57; "H$_{5,6}$=" should read -- H$_5$, J$_{5,6}$= --
Column 26, line 24; "-I,4-" should read -- -1,4- --
Column 26, linne 46; "175" should read -- 1175 --
Column 26, line 51; "-I,4-" should read -- -1,4- --
Column 26, line 68; "H$_8$,J$_{8,6}$=2.9Hz);8.7" should read -- H$_6$,J$_{6,8}$=2.9Hz,J$_{6,5}$=8.7Hz) --
Column 27, line 28; "333" should read -- 3 x --.
Column 27, line 29; "J$_{6,5}$8.33" should read -- J$_{6,5}$=8.33 --
Column 27, line 33; "(=C-O-)" should read -- (=C-O-C) --
Column 30, line 57; ",J$_5$.," should read -- ,H$_5$., --
Column 30, line 58; "8.36" should read -- 8.63 --
Column 30, line 60; "6.28d," should read -- 6.28(d, --

UNITED STATES PATENT AND TRADEMARK OFFICE
CERTIFICATE OF CORRECTION

PATENT NO. : 5,420,132

DATED : May 30, 1995

INVENTOR(S) : Gèrald Guillaumet, Gèrard Coudert, Valèrie Thiery, Gèrard Adam, Jean-Guy-Bizot-Espiard, Bruno Pfeiffer, Pierre Renard It is certified that error appears in the above-indentified patent and that said Letters Patent is hereby corrected as shown below:

Column 32, line 24; "$J_{6'',2''}$" should read -- $J_{6'',2''}$ --
Column 32, line 26; "$_{=2}Hz$);" should read -- =2 Hz); --
Column 32, line 58; "$H_{2'},$" should read -- $H_{2'},$ --
Column 32, line 61; "$H_{5'},$" should read -- $H_{5'},$ --
Column 33, line 46; the "R" at the bottom of the formula should read -- F --
Column 34, line 20; "=11.4$J_3$=' should read -- =$H_2, J_3$= --
Column 35, line 36; "{4-UBIS-" should read -- {4-[BIS- --
Column 36, line 57; "-2-14-" should read -- -2-{4- --
Column 37, line 68; "$H_{5,7}$=" should read -- $H_5, J_{5,7}$= --
Column 41, line 44; "µ/ml)" should read -- µg/ml) --
Column 41, line 47; (50 µ/ml)." should read -- (50 µg/ml). --
Column 46, line 21; insert a -- : -- after the word "proviso"
Column 46, line 22; insert a comma "," between "hydrogen" and "$R_9$"

Signed and Sealed this

Seventeenth Day of October, 1995

BRUCE LEHMAN

*Attest:*

*Attesting Officer*   Commissioner of Patents and Trademarks